United States Patent [19]

Chiu et al.

[11] Patent Number: 4,916,214

[45] Date of Patent: Apr. 10, 1990

[54] CATIONIC COMPLEXES OF TECHNETIUM-99M

[75] Inventors: Kwok W. Chiu; James D. Kelly, both of Buckinghamshire; Ian A. Latham, Nottingham; David V. Griffiths, Staffordshire, all of England; Peter G. Edwards, Cardiff, Scotland

[73] Assignee: Amersham International plc., Little Chalfont, England

[21] Appl. No.: 254,082

[22] Filed: Oct. 6, 1988

[30] Foreign Application Priority Data

Oct. 6, 1987 [GB] United Kingdom ............... 8723438

[51] Int. Cl.[4] ............... A61K 43/00; A61K 49/00; C07B 59/00; C07F 13/00
[52] U.S. Cl. ........................................ 534/14; 424/1.1
[58] Field of Search ............................. 534/14; 424/1.1

[56] References Cited

U.S. PATENT DOCUMENTS

| 4,374,821 | 2/1983 | Glavan et al. | 534/14 X |
|---|---|---|---|
| 4,387,087 | 6/1983 | Deutsch et al. | 534/14 X |
| 4,451,450 | 5/1984 | Subramanyam | 424/1.1 |
| 4,481,184 | 11/1984 | Kronauge et al. | 424/1.1 |
| 4,489,054 | 12/1984 | Deutsch et al. | 424/1.1 |
| 4,526,776 | 7/1985 | Subramanyam et al. | 424/1.1 |
| 4,765,971 | 8/1988 | Wester et al. | 534/14 X |
| 4,781,912 | 11/1988 | Zanelli et al. | 534/14 X |
| 4,795,626 | 1/1989 | Deutsch et al. | 534/14 X |

FOREIGN PATENT DOCUMENTS 0038756 10/1981 European Pat. Off.
1917884 10/1969 Fed. Rep. of Germany.

OTHER PUBLICATIONS

Bartsch et al., "Inorg. Chem", 23, 3304–3309 (1984).

*Primary Examiner*—Stephen J. Lechert, Jr.
*Assistant Examiner*—Virginia B. Caress
*Attorney, Agent, or Firm*—Wenderoth, Lind & Ponack

[57] ABSTRACT

The invention concerns cationic complexes of Technetium-99m with bidentate ligands (L), including complexes having the formulae $[Tc(NO) X L_2]^+$ and $[Tc L_3]^+$, which are of interest as heart imaging agents. The ligands are characterized by having the formula $Y_2Q\text{-}ZQY_2$, where each Q is phosphorus or arsenic, Z is a 2 or 3 carbon atom linking group, and at least one of the groups Y and Z includes at least one —COC—ether group.

5 Claims, No Drawings

CATIONIC COMPLEXES OF TECHNETIUM-99M

This invention relates to cationic complexes of technetium-99m (Tc-99m) useful as body imaging agents.

Radiopharmaceuticals may be used as diagnostic or therapeutic agents by virtue of the physical properties of their constituent radionuclides. Thus, their utility is not based on any pharmacologic action. Most clinically used drugs of this class are diagnostic agents incorporating a gamma-emitting nuclide which because of physical or metabolic properties of its co-ordinated ligands, localises in a specific organ after intravenous injection. The resultant images can reflect organ structure or function. These images are obtained by means of a gamma camera that detects the distribution of ionising radiation emitted by the radioactive molecules. The principal isotope currently used in clinical diagnostic nuclear medicine is metastable technetium-99m ($t_{\frac{1}{2}}$ 6 hours).

It is well established that neutral bidentate ligands of the general type $R_2Q(CH_2)_nQR_2$ (where Q may be phosphorus or arsenic, and n is 2) form stable well characterised cationic complexes with $^{99}Tc$ and $^{99m}Tc$[1]. Several patents, including U.S. Pat. Nos. 4,481,184, 4,387,087, 4,489,054, 4,374,821, 4,451,450 and 4,526,776 describe various ligand species in which the co-ordinating atoms are phosphorus or arsenic, with predominantly alkyl and/or aryl substituents.

The present invention concerns neutral bidentate donor ligands based on Phosphorus or Arsenic and which contain ether linkages; and cationic complexes of Tc-99m comprising these ligands. It is found that such complexes show surprising properties which may make them superior body imaging agents, particularly heart imaging agents, to comparable complexes not containing ether linkages.

In one aspect the invention provides a ligand having the formula:

$$Y_2QZQY_2$$

where each Q is phosphorus or arsenic, the groups Y may be the same or different and each is H or C1–C8 saturated hydrocarbon or saturated fluorohydrocarbon which may contain up to 3 ether oxygen atoms.

Z is a —CC— or —CCC— or —COC— chain or an o-phenylene which may be substituted by at least one C1–C8 saturated hydrocarbon or saturated fluorohydrocarbon group which may contain up to 3 ether oxygen atoms, provided that the ligand contains at least one —COC— ether linkage. Preferably, the ligand contains 2 or 3 —COC— ether linkages.

Examples of C1–C8 saturated hydrocarbon groups optionally containing up to 3 ether oxygen atoms are
Alkyl
Cyclohexyl
Alkoxy
Alkoxyalkyl
Alkoxyalkoxyalkyl
Alkoxyalkoxyalkoxyalkyl
—CH$_2$OC(CH$_3$)$_2$OCH$_2$—
—CH$_2$CH$_2$OCH$_2$CH$_2$—
2-Tetrahydrofuryl Saturated fluorohydrocarbon groups may be, for example, any of the above in which one or more hydrogen atoms are replaced by fluorine atoms.

The groups Y may be the same of different and each is preferably H or C1–C4 alkyl which may be substituted by C1–C4 alkoxy. Those groups Y which contain no ether oxygen atom are preferably H, methyl or ethyl. Z is preferably a —CC— or —CCC— or —COC— chain which may be substituted by C1–C4 alkoxy or alkoxyalkyl or spirocyclic ether.

More preferably each Q is phosphorus, Z is a —CC—or —CCC— chain, each Y is H or methyl, and either one or more methoxy substituents is attached to one or more groups Y, or one or more methoxymethyl or —COC— spirocyclic ether groups is attached to a carbon atom of Z.

In another aspect of the invention provides a cationic complex of Tc-99m with the ligand as defined. The cationic complex preferably has a formula selected from:

$$[Tc(NO)_nX_mL_2]^+A^-$$

and $$[TcL_3]^+A^-$$

where
X is a monodentate ligand for Tc
A an is anion
n is 1 or 2 and m is correspondingly 1 or 0, and
L is the ligand.

In the cationic complexes, X is a monodentate ligand for Tc, generally a halide such as F, Cl, Br or I, or a pseudohalide such as SCN, N$_3$, CN or RS. A is an anion whose nature is not critical, but which may conveniently be selected from the list given for X.

The ligand is characterised by containing at least one —COC— ether linkage. This may be provided by means of a —COC— chain linking the two arsenic or phosphorus atoms. More usually, the ether linkage is provided by means of an alkoxy or alkoxyalkyl substituent on one or more of the groups Y and Z. Preferably, Z is a —CC— or —CCC— chain, each Y is a H or methyl, and one or more methoxy or methoxymethyl substituents is attached to one or more groups Y or Z. Various substitution patterns are envisaged, for example:

(a) Backbone substitution which may be single or multiple for example:

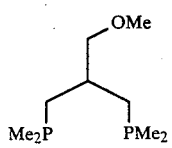

(i)

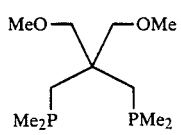

(ii)

(b) Phosphorus functionalisation which may be unsymmetrical or symmetrical for example:

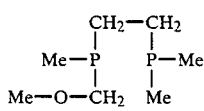

(i)

-continued

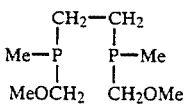

(c) A mixture of functionalisation at the phosphorus atom and in the backbone.
(d) The spirocyclic type, for example:

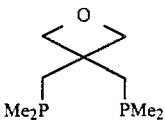

In all these examples, P may be replaced by As.

As indicated in the Examples below, these cationic complexes of Tc-99m are of interest as heart imaging agents. The size of the groups Y and Z, and the number and size of the alkoxy, alkoxyalkyl or spirocyclic ether substituents, can be chosen to make the complex as lipophilic as may be desired for this purpose (or for any other purpose for which the complexes are to be used). But the ether linkages are not there merely to provide a desired hydrophilic/lipophilic balance. It has surprisingly been found that complexes formed from ligands with an ether linkage have significantly higher heart uptake than similarly hydrophobic complexes formed from corresponding ligands without an ether linkage. It appears that the ether linkages in the ligand modify the biological behaviour of the Tc-99m complex, compared to the unsubstituted analogue, by providing increased blood and liver clearance which are essential to achieve good target organ to background ratios.

Preferred cationic complexes technetium-99m with bidentate ligands of this invention have formulae:

[Tc(NO)XL$_2$]$^+$A$^-$  (a)

where
X is a monodentate ligand for Tc,
A is an anion, and
L is a ligand having the formula

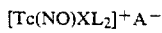
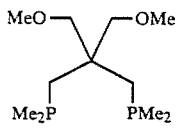

[TcL$_3$]$^+$A$^-$  (b)

where L is a ligand having the formula

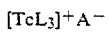
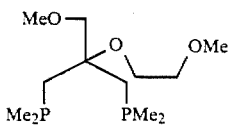

Although this invention is concerned with results rather than with mechanisms, applicants offer the following as a possible explanation of mechanisms. Broadly, for compounds of similar structure, there is a relationship between lipophilicity and protein binding. Compounds of high lipophilicity are more strongly bound to proteins than compounds of low lipophilicity.

For $^{99m}$Tc cations, the effect of high protein binding is that they remain a long time in circulation, so that the image of the heart muscle at convenient imaging times post-injection is obscured by the blood pool activity. A further generally observed tendency for the more highly lipophilic cations is that they possess slow clearance through the hepatobiliary system, so that heart imaging can be impaired by liver activity.

Substantially increasing the hydrophilicity of a $^{99m}$Tc complex has the desired effect reducing protein binding but also reduces heart uptake. It appears that there is, however, a region of intermediate lipophilicity where the heart uptake is retained and there is also absent, or sufficiently weak, protein binding to permit rapid clearance from blood.

It appears that there may be a ranking in contribution to polarity of TcO greater than MeO greater than EtO. By means of this background understanding, it may be possible to achieve the required lipophilic/hydrophilic balance through the additive hydrophilic effects of the oxygen substituents balancing out the lipophilic effects of the hydrocarbon moieties in the molecule.

These phosphine and arsine ligands are not easy to make. They are toxic, the compounds or their precursors often spontaneously flammable in air and their preparation frequently entails hazards of explosion or difficult to control reactions. Conditions may need to be carefully chosen to avoid the risk of side-reactions. The following reaction schemes are available:

A. MeP(CH$_2$OMe)—(CH$_2$)$_2$—P(Me)(CH$_2$OMe)

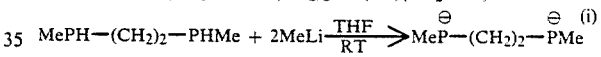
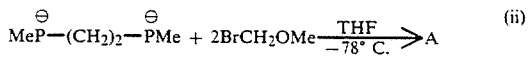

This route is available for other symmetrical ligands which are mono-substituted at each P (or As) atom.

B. Me$_2$P—(CH$_2$)$_2$—P(Me)(CH$_2$OMe)

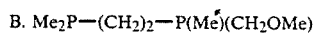
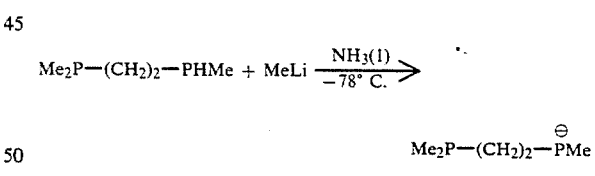

or

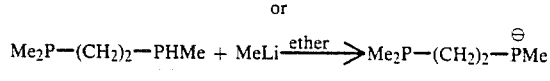

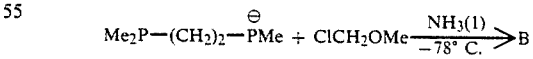

This route is available for other unsymmetrical ligands which are mono-substituted at one P (or As) atom.

C. Me$_2$P—CH$_2$—CH(CH$_2$OMe)—CH$_2$—PMe$_2$

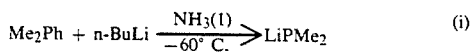

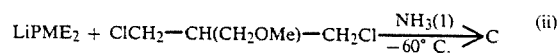

This route is available for other ligands where the backbone is substituted by alkoxy or alkoxyalkyl or spirocyclic ether.

These and other routes are described in more detail in Examples 1, 2 and 8 to 12 below.

The cationic complexes of Tc-99m may be prepared by methods well known in the art. For example:

Complexes of the type [TcX$_2$L$_2$]$^+$A$^-$ may be prepared by methods as described in U.S. Pat. Nos. 4,387,087 and 4,489,054.

Complexes of the type [Tc(NO)$_n$X$_m$L$_2$]$^+$A$^-$ may be prepared by methods as described in European patent application No. 88,304,239.2.

Complexes of the type [TcL$_3$]$^+$A$^-$ may be prepared by methods as described in U.S. Pat. No. 4,481,184.

The following Examples illustrate the invention.

SYNTHESIS OF METHYLETHER SUBSTITUTED DIPHOSPHINES

All reactions and manipulations were performed under vacuo or oxygen free nitrogen atmospheres. Solvents were dried and degassed by nitrogen purge or freeze/thaw cycles prior to use. The reagents BrCH$_2$OMe and ClCH$_2$OMe were purchased or obtained from Amersham (BrCH$_2$OMe and ClCH$_2$OMe were distilled prior to use) and were deoxygenated by freeze thaw cycles. MeLi was prepared from MeCl in diethylether and was estimated and used in diethylether solution. Ammonia was dried by distillation from sodium. The phosphines MePH-(CH$_2$)$_2$-HPMe [Ref. 1], and Me$_2$P-PMe$_2$ [Ref. 2] were prepared according to established procedures. Me$_2$P(CH$_2$)$_2$P(H)Me [Ref. 3] was prepared from Me$_2$P(CH$_2$)$_2$PH$_2$ [Ref. 4]. Abbreviations used are: THF=tetrahydrofuran; R.T.=ambient temperature; ether=diethylether=Et$_2$O; Me=methyl.

EXAMPLE 1

MeP(CH$_2$OMe)-(CH$_2$)$_2$-(Me)P(CH$_2$OMe)

(See reaction scheme A above)

Procedure:

To a 250 ml 3 neck round bottom flask equipped with a condenser, a pressure equalising dropping funnel and a magnetic stirrer, was transferred the phosphine MePH-(CH$_2$)$_2$-PHMe, ((6.76 g; 5.53×10$^{-2}$ moles) in 35 ml THF. MeLi (11.67×10$^{-2}$ moles in ether solution) was taken into the dropping funnel and added dropwise to the phosphine with stirring at room temperature, which changed colour to light yellow. The dropping funnel was rinsed with 10 cm$^3$ THF and charged with BrCH$_2$OMe (13.83 g, 11.07×10$^{-2}$ moles) in 20 ml of THF. The reaction flask was cooled to −78° C. and the solution of BrCH$_2$OMe was added dropwise with stirring, stirred at this temperature for 1 h, and allowed to warm to room temperature. The resulting suspension was hydrolysed, the organic layer separated and dried over magnesium sulphate overnight. The dried organic layer was distilled. As the temperature was raised gradually, ether together with the THF distilled at 38°–70° C. Finally, the product distilled at 74°–82° C. under dynamic vacuum (about 0.1 mm Hg) as a colourless liquid.

Yield=2.96 g (25.5%).

EXAMPLE 2

Me$_2$P-(CH$_2$)$_2$-P(Me) (CH$_2$OMe)

(See reaction scheme B above)

Procedure 1:

In a 250 ml 3 neck round bottom flask, equipped with a dry ice condenser (with a T-adapter at the top as the N$_2$ inlet-outlet system), a pressure equalising dropping funnel and a magnetic stirrer, was condensed about 150 ml anhydrous liquid ammonia.

The liquid ammonia was kept at −78° C. and the phosphine Me$_2$P-(CH$_2$)$_2$-PHMe (2.06 g; 1.51×10$^{-2}$ moles) was transferred into the reaction flask. Required amount of MeLi (1.51×10$^{-2}$ moles) was added dropwise to the phosphine from the dropping funnel, which produced a deep orange colour. The dropping funnel was rinsed with 10 ml ether and charged with a solution of ClCH$_2$OMe (1.22 g, 1.51×10$^{-2}$ moles) in 20 ml ether. This solution was added dropwise to the reaction mixture until the deep orange colour disappeared. The reaction mixture was allowed to warm to room temperature and after the ammonia had evaporated, about 50 ml ether was added and the resulting slurry hydrolysed. The ether layer was removed, dried over magnesium sulphate overnight. The dried ether layer was distilled and after removing ether, the product distills at approx. 80° C. under dynamic vacuum (0.1 mmHg) as a colourless liquid.

Yield=0.61 g (22.5%).

Procedure 2:

Note: As the starting phosphine Me$_2$P-(CH$_2$)$_2$-PHMe was contaminated with a small amount of Me$_2$P-(CH$_2$)$_2$-PMe$_2$, it was purified by precipitation of the salt Me$_2$P-(CH$_2$)$_2$-PMeLi by reaction with MeLi in ether, which would keep Me$_2$P-(CH$_2$)$_2$-PMe$_2$ in solution and enable easy removal.

In a 500 ml 3 neck flask equipped with dry ice condenser (with a T adapter at the top as N$_2$ inlet-outlet system), a pressure equalising dropping funnel and a magnetic stirrer, was transferred the phosphine Me$_2$P-(CH$_2$)$_2$-PHMe (4.9 g; 3.6×10$^{-2}$ mole) in 30 ml ether. MeLi (3.6×10$^{-2}$ moles in ether) was added dropwise from the dropping funnel to the phosphine solution. As there was no immediate precipitation, most of the ether was evaporated when precipitation occured. The remaining solution was filtered off, and the precipitate was washed twice with 10 ml portions of ether. The reaction flask was then cooled to −78° C. and about 200 ml anhydrous liquid ammonia was condensed to the reaction flask. The precipitated colourless solid forms an orange slurry in contact with liquid ammonia. The dropping funnel was rinsed with 10 ml portions of ether and charged with a solution of ClCH$_2$OMe (2.9 g; 3.60×10$^{-2}$ moles) in 20 ml ether. This solution was added dropwise to the stirred orange slurry until the colour just disappears. The reaction mixture was allowed warm to room temperature and after all the ammonia has evaporated, about 50 ml ether was added and the resulting slurry was hydrolysed. The ether layer was separated, dried over magnesium sulphate overnight. The dried ether layer was distilled and after removing ether, the product distills at about 80° C./dynamic vacuum (0.1 mm Hg) as a colourless liquid. As the product contained traces of water, it was dried over KOH for 4 h and redistilled.

Amount=1.7 g (26%).

REFERENCES

1. M. Baake, O. Stelzer and V. Wray, Chem. Ber., 113, 1356 (1980); or by addition of MeI (2 mole equivalents) to $H_2P(CH_2)_2PH_2$ in methanol or ethanol followed by isolation of the disphosphonium salt $[Me_2P(H_2)\text{-}(CH_2)_2\text{-}P(H_2)Me]^{2+}.2I^-$ and liberation of the free disecondary phosphine by neutralisation.
2. D. W. Meek et al., Inorg. Synth., 14, 15 (1973).
3. Prepared by deprotonation of $Me_2P(CH_2)_2PH_2$ with either MeLi or Bun[n]Li in ether or hydrocarbon solvents followed by formation of the required tertiarty-secondary phosphine by addition of MeI.
4. R. B. King and J. C. Cloyd, J. Amer. Chem. Soc., 97, 46 (1975). R. C. Taylor and D. B. Walters, Inorg. Synth., 1973, 14, 10.

$^1$H NMR data (360 MHz)

$^1$H NMR spectra were recorded on a Bruker WH360 operating at 360 MHz and were referenced on the protio impurity of the $C_6D_6$ used as solvent (7.27 ppm).

| Phosphines/Assignments | | | | |
|---|---|---|---|---|
| P-Me | P—CH$_2$O | P—CH$_2$—CH$_2$—P | | O-Me |
| MeOCH$_2$P(Me)—(CH$_2$)$_2$—P(Me) (CH$_2$OMe) | | | | |
| 1.05H 6H | 3.55[1] 4H | 1.55[1], 1.82[1] 4H | | 3.22(s) 6H |
| Me$_2$P—(CH$_2$)$_2$—P(Me) (CH$_2$OMe) | | | | |
| .92(d) 6H 1.01(d) 3H | 3.52[2] 2H | 1.35–1.5[1] 4H | | 3.24(s) 3H |

Mass Spectrometry Data
MeOCH$_2$P(Me)—(CH$_2$)$_2$—P(Me) (CH$_2$OMe)
MW = 210

| | | |
|---|---|---|
| M.+ | 210 | |
| M-15 | [MeOCH$_2$P(Me)—(CH$_2$)$_2$—P(CH$_2$OMe)]+ | 195 |
| M-45 | [MeOCH$_2$P(Me)—(CH$_2$)$_2$—P(Me)]+ | 165 |
| M-105 | [MeOCH$_2$P(Me)—CH$_2$]+ | 105 |
| M-165 | [MeOCH$_2$]+ | 45 base peak |

IR Data
MeOCH$_2$P(Me)—(CH$_2$)$_2$—P(Me) (CH$_2$OMe)
(Neat)

| | | | | |
|---|---|---|---|---|
| 2900(m) | 2810(m) | 1465(w) | 1450(w) | 1425(m) |
| 1310(w) | 1280(w) | 1180(m) | 1090(s) | 950(m) |
| 700(m) | | | | |

[1]Complicated multiplet
[2]Quintet

B. SYNTHESIS AND PROPERTIES OF CATIONIC TECHNETIUM-99m COMPLEXES OF LIGANDS OF EXAMPLES 1 AND 2

EXAMPLE 3

$[TcX_2L_2]$ = Technetium III disphosphine dihalide complex

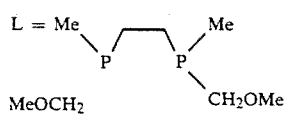

Materials 8 mg EGTA
120 mg NaCl
3 mg FeCl$_3$/6μl L/1 ml EtOH
1.1 ml $^{99m}$-TcO$_4^-$ Na generator eluate (at 1.49 GBq/ml)

These constituents were placed in a sealed glass vial under N$_2$ and heated at 120° C. for 70 minutes, to which 3 ml of 50% EtOH=saline, and 0.15 ml 1M KHCO$_3$ were added, final ph=6. The resulting solution was submitted to various analytical techniques, summarised below.

Chromatography Data

The resulting solution (above) contains no free $^{99m}$TcO$_4^-$ and no colloid, and indicates that the technetium complex is present in solution in approximately 95% yield.

| | |
|---|---|
| Saline | rf = 0.88 |
| Methylethylketone | rf = +0.76 |
| Acetonitrile/water 50:50 | rf = 0.80 (broad) |

Gel Electrophoresis Data

The complex moved as a single band towards the cathode rf= −0.53 (− indicating movement towards the cathode).

HPLC Data

The compound elutes as a single band with a retention time of approximately 7.0 minutes.

EXAMPLE 4

Synthesis of $[Tc(NO)X(L)_2]=X^-$ Nitrosyl Complex X=Cl L=

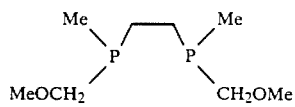

| Materials | |
|---|---|
| NH$_2$OH.HCl | 2.5 mg |
| SnF$_2$ | 0.8 ml at 6.6 × 10$^{-5}$ M solution (aq.) |
| L | 5 μl |
| $^{99m}$TcO$_4$Na | generator eluate at 316 mCi/ml |
| Saline | 0.4 ml |

Method

The components were mixed in a sealed, N$_2$ purged vial and heated at 120° C. for 1 hour. The crude preparation was then subjected to HPLC purification and the major component (retention time 6.3 minutes) collected, any remaining THF was removed and the resulting solution analysed in the usual way. A sample of this material was submitted for animal biodistribution studies, final pH=7.4.

Chromatography

The resulting preparation contains no colloid or free TcO$_4^-$, and indicates that the desired species is present in approximately 85% yield.

| | |
|---|---|
| Saline | rf = 0.02 |

| -continued | |
|---|---|
| Methylethylketone | rf = 0.69 |
| Acetonitrile:Water, 50:50 | rf = 1.0 |

Gel Electrophoresis

The complex moves as a single band towards the cathode rf=−0.75 (− indicates movement towards cathode).

HPLC Data

The complex elutes as a single band with a retention time of approximately 6.3 minutes.

Animal Biodistribution Data

See Table I.

TABLE I $[Tc^I(NO)X(L)_2]^+Cl^-$
Animal Biodistribution Data in Rats

L = Me\P/\P/Me with MeOCH$_2$ and CH$_2$OMe

| | Time p.i. in vivo | | | |
|---|---|---|---|---|
| | 2 min | | 60 min | |
| | m | sd | m | sd |
| % Injected Dose/Organ | | | | |
| Heart | 1.71 | 0.40 | 1.42 | 0.18 |
| Blood | 6.63 | 3.09 | 0.79 | 0.08 |
| Muscle | 22.0 | 7.7 | 27.1 | 1.8 |
| Lung | 1.85 | 0.18 | 0.83 | 0.12 |
| Liver | 12.6 | 3.2 | 1.53 | 0.06 |
| Liver + GI | 33.5 | 7.2 | 40.1 | 0.2 |
| Kidney + U | 10.9 | 2.0 | 12.86 | 1.2 |
| Counts/Gram Ratio | | | | |
| Heart/Blood | 4.19 | 1.81 | 25.7 | 6.4 |
| Heart/Muscle | 6.61 | 1.15 | 5.46 | 0.42 |
| Heart/Liver | 1.81 | 0.72 | 10.8 | 1.4 |
| Heart/Lung | 1.5 | 0.1 | 2.6 | 0.2 |

EXAMPLE 5

Synthesis of $[Tc(L)_3]^=X^-$ tris phosphine-complex
X=Cl L=

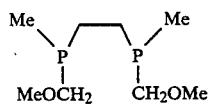

| Materials | |
|---|---|
| Ethanol | 2 ml |
| NaOH | 0.05 ml, 10M aq. solution |
| Saline | 0.6 ml |
| L | 20 μl |
| $^{99m}TcO_4Na$ | Generator Eluate 0.4 ml at 3.73 GBq/ml |

Method

The components were mixed in a sealed, N$_2$ purged vial and heated at 120° C. for 30 minutes. This solution was then diluted with 3 ml 66% saline/ethanol, and the pH adjusted to 6 with 0.1M HCl. The resulting solution was then submitted to chromatographic analysis and animal biodistribution study.

Chromatographic Data

The resulting preparation contains no free $TcO_4^-$ or reduced technetium colloid, and indicates that the desired species is present in solution approximately 90% yield.

| Saline | rf = 0.00 |
|---|---|
| Methylethylketone | rf = 0.75 (broad) |
| Acetonitrile:Water 50:50 | rf = 0.98 |

HPLC Data

The complex elutes as a sharp band at approximately 8.1 minutes (∼10% minor component at ∼6 minutes=10%).

Animal Biodistribution Data

See Tables II and III

TABLE II $[Tc^I(L)_3]^+X^-$ Animal Biodistribution in Rats
L = Me\P/\P/Me with MeOCH$_2$ and CH$_2$OMe

| | Time p.i. in vivo | | | |
|---|---|---|---|---|
| | 2 min | | 60 min | |
| | m | sd | m | sd |
| % Injected Dose/Organ | | | | |
| Heart | 1.28 | 0.08 | 1.06 | 0.12 |
| Blood | 5.60 | 0.45 | 0.58 | 0.20 |
| Muscle | 21.4 | 2.4 | 19.6 | 3.9 |
| Lung | 2.79 | 0.10 | 1.17 | 0.37 |
| Liver | 25.3 | 1.7 | 9.32 | 0.60 |
| Liver + GI | 42.6 | 3.1 | 50.2 | 4.5 |
| Kidney + U | 9.78 | 1.15 | 14.1 | 2.0 |
| Counts/Gram Ratio | | | | |
| Heart/Blood | 3.12 | 0.37 | 30.5 | 5.4 |
| Heart/Muscle | 6.09 | 0.97 | 6.43 | 0.82 |
| Heart/Liver | 0.60 | 0.06 | 1.50 | 0.30 |
| Heart/Lung | 0.7 | 0.0 | 1.7 | 0.3 |

TABLE III $[Tc(L)_3]^+X^\ominus$ Animal Biodistribution in Guinea Pigs
L = Me\P/\P/Me with MeOCH$_2$ and CH$_2$OMe    X = Cl

| | Time p.i. in vivo | | | |
|---|---|---|---|---|
| | 2 min | | 60 min | |
| | Mean | Std. dev. | Mean | Std. dev. |
| | % Injected dose/organ | | | |
| Heart | 0.98 | 0.23 | 0.83 | 0.13 |
| Blood | 14.4 | 2.6 | 1.83 | 0.36 |
| Muscle | 16.3 | 3.7 | 26.5 | 7.6 |
| Lung | 3.54 | 0.68 | 0.88 | 0.17 |
| Liver | 24.0 | 4.0 | 13.3 | 1.6 |
| Liver + GI | 40.4 | 5.5 | 47.3 | 5.4 |
| Kidney + Urine | 11.6 | 2.3 | 16.3 | 0.4 |
| | Counts/Gram ratio | | | |
| Heart/Blood | 1.63 | 0.21 | 10.5 | 1.20 |
| Heart/Muscle | 8.18 | 1.78 | 4.29 | 1.60 |
| Heart/Liver | 0.82 | 0.50 | 0.72 | 0.08 |
| Heart/Lung | 0.2 | 0.00 | 0.9 | 0.1 |

Example 6

Synthesis of [Tc(NO) X (L)$_2$]=X$^-$ Nitrosyl Complex

Where X=Cl L=

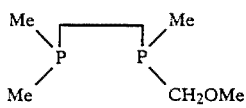

| Materials | |
|---|---|
| NH$_2$OH.HCl | 25 mg |
| SnF$_2$ | 1.0 ml 8 μg/ml |
| L | 10 μl |
| $^{99m}$TcO$_4$Na | 1.2 ml at 243 mCi/ml (generator eluate) |

Method

The components were mixed in a sealed N$_2$ purged vial and heated at 120° C. for 1 hour. The crude preparation was then subjected to HPLC purification and the major component (retention time 6.5 minutes) collected, any remaining THF was removed and the resulting solution analysed in the usual way. A sample of this material was submitted for animal biodistribution studies, final pH=7.4.

Chromatography

The resulting preparation contains no reduced technetium colloid or free TcO$_4^-$, and indicates that the desired species is present in approximately 95% yield.

| | |
|---|---|
| Saline | rf = 0.04 |
| Methylethylketone | rf = 0.86 |
| Acetonitrile:water 50:50 | rf = 0.90 |

Gel Electrophoresis Data

The complex moves as a single band towards the cathode rf=−0.78 (− indicates movement towards the cathode).

HPLC Data

This complex elutes as a single band, with a retention time of approximately 6.5 minutes.

Animal Biodistribution Data

See Table IV

TABLE IV

Animal Biodistribution Data
[Tc(NO)Cl(L)$_2$]$^+$ (in rats)

L = 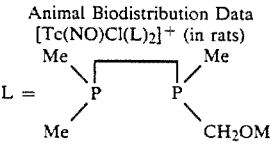

| | Time p.i. in vivo | | | |
|---|---|---|---|---|
| | 2 min | | 60 min | |
| | Mean | Std. dev. | Mean | Std. dev. |
| | % Injected dose/organ | | | |
| Heart | 0.96 | 0.05 | 0.94 | 0.11 |
| Blood | 1.77 | 0.18 | 0.26 | 0.02 |
| Muscle | 21.83 | 0.88 | 23.70 | 2.30 |
| Lung | 0.92 | 0.15 | 0.63 | 0.17 |
| Liver | 20.45 | 1.28 | 1.62 | 0.39 |
| Liver + GI | 43.70 | 2.96 | 51.11 | 5.8 |

TABLE IV-continued

Animal Biodistribution Data
[Tc(NO)Cl(L)$_2$]$^+$ (in rats)

L = 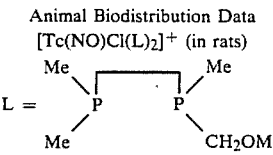

| | Time p.i. in vivo | | | |
|---|---|---|---|---|
| | 2 min | | 60 min | |
| | Mean | Std. dev. | Mean | Std. dev. |
| Kindney + Urine | 15.40 | 1.31 | 14.48 | 0.49 |
| | Counts/Gram ratio | | | |
| Heart/Blood | 9.05 | 8.10 | 49.63 | 3.74 |
| Heart/Muscle | 4.99 | 4.58 | 4.17 | 0.34 |
| Heart/Liver | 0.57 | 0.62 | 7.26 | 0.75 |
| Heart/Lung | | | | |

Example 7

Synthesis of [Tc(L)$_3$]=X$^-$ Tris-diphosphine Complex

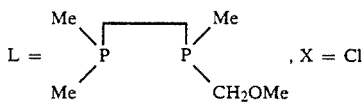, X = Cl

| Materials | |
|---|---|
| Ethanol | 1 ml |
| NaOH | 0.05 ml, 10M aq. solution |
| Saline | 2 ml |
| L | 10 μl |
| $^{99m}$TcO$_4$Na | Generator Eluate 0.5 ml at 2.66 GBq/ml |

Method

The components were mixed in a sealed N$_2$ purged vial and heated at 120° C. for 30 minutes; pH of the solution was adjusted to 7-8 with 0.1M HCl. The resulting solution was them submitted to chromatographic analysis and animal biodistribution study.

Chromatography

The resulting preparation contains no free TcO$_4^-$ or reduced technetium colloid, and indicates that the desired species is present in approximately 95% yield.

| | |
|---|---|
| Saline | rf = 0.00 |
| Methylethylketone | rf = 0.67 |
| Acetonitrile:water 50:50 | rf = 0.75 |

HPLC Data

This complex elutes as a sharp peak at approximately 8.4 minutes (5% minor components between 4.5 to 6 minutes).

Animal Biodistribution Data

See Tables V and VI

TABLE V

Animal Biodistribution Data in Rats $[Tc^I(L)_3]^+X^\ominus$

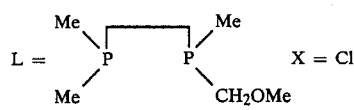

L = (Me)(Me)P–P(Me)(CH$_2$OMe), X = Cl

| Time p.i. in vivo | 2 min | | 60 min | |
|---|---|---|---|---|
| | % Injected dose/organ | | | |
| | Mean | Std. dev. | Mean | Std. dev. |
| Heart | 1.37 | 0.07 | 0.95 | 0.12 |
| Blood | 6.19 | 0.45 | 0.50 | 0.07 |
| Muscle | 25.7 | 1.9 | 18.4 | 0.26 |
| Lung | 3.08 | 0.24 | 1.22 | 0.26 |
| Liver | 20.5 | 1.5 | 10.3 | 1.0 |
| Liver + GI | 34.7 | 2.7 | 47.7 | 0.8 |
| Kidney + Urine | 11.0 | 1.2 | 16.0 | 1.3 |
| | Counts/Gram ratio | | | |
| Heart/Blood | 2.99 | 0.58 | 29.5 | 4.5 |
| Heart/Muscle | 5.32 | 1.02 | 5.90 | 0.99 |
| Heart/Liver | 0.87 | 0.14 | 1.41 | 0.21 |
| Heart/Lung | 0.60 | 0.20 | 1.2 | 0.2 |

TABLE VI

Animal Biodistribution Data in Guinea Pigs $[Tc(L)_3]^\oplus X^\ominus$

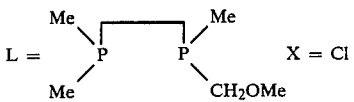

L = (Me)(Me)P–P(Me)(CH$_2$OMe), X = Cl

| Time p.i. in vivo | 2 min | | 60 min | |
|---|---|---|---|---|
| | % Injected dose/organ | | | |
| | Mean | Std. dev. | Mean | Std. dev. |
| Heart | 0.96 | 0.34 | 0.43 | 0.11 |
| Blood | 15.24 | 2.79 | 1.24 | 0.23 |
| Muscle | 12.98 | 2.0 | 12.03 | 4.00 |
| Lung | 3.58 | 0.52 | 0.74 | 0.17 |
| Liver | 24.85 | 2.28 | 26.13 | 5.02 |
| Liver + GI | 40.7 | 3.18 | 61.7 | 6.03 |
| Kidney + Urine | 13.6 | 4.56 | 17.1 | 2.77 |
| | Counts/Gram ratio | | | |
| Heart/Blood | 1.59 | 0.41 | 7.82 | 1.07 |
| Heart/Muscle | 9.19 | 0.60 | 4.60 | 0.58 |
| Heart/Liver | 0.51 | 0.08 | 0.30 | 0.12 |
| Heart/Lung | 0.28 | 0.04 | 0.44 | 0.08 |

Comparative Data

The bidentate phosphine ligand di(dimethylphosphino) ethane (dmpe) is well known, and various Tc-99m complexes have been proposed for use as heart imaging agents. The following Tables VII, and VIII compare the biodistribution data of two such prior art complexes with the data given above in respect of the complexes of Example 4, 5, 6 and 7 (derived from the ligands of Example 1 and 2). The Tables permit the following conclusion.

From Table VII, the complex formed from the ligand of Example 1 shows:
(i) significantly higher heart uptake and retention at 2' and 60'
(ii) reduced liver retention at 60'
(iii) significantly increased heart/liver ratio at 60'.

From Table VIII, the complex formed from the ligand of Example 1 shows:
(i) increased heart uptake and retention at 2' and 60'
(ii) much lower liver retention at 60'
(iii) better heart/blood, heart/muscle and heart/liver ratios at 60'.

Complexes formed from the ligand of Example 2 show the same general trend.

TABLE VII $[Tc(NO)Cl_2L_2]^-$ in Rats

| Ligand | Organ or Ratio | 2 min p.i. | 60 min p.i. |
|---|---|---|---|
| | | % injected dose | |
| dmpe | Heart | 0.46 | 0.32 |
| | Liver | 24.92 | 3.05 |
| | | Counts/Gram ratio | |
| | Heart/Blood | 1.71 | 24.18 |
| | Heart/Muscle | 1.84 | 2.08 |
| | Heart/Liver | 0.24 | 1.52 |
| | | % injected dose | |
| Ex. 1 | Heart | 1.71 | 1.42 |
| | Liver | 12.6 | 1.53 |
| | | Counts/Gram ratio | |
| | Heart/Blood | 4.19 | 25.7 |
| | Heart/Muscle | 6.61 | 5.46 |
| | Heart/Liver | 1.81 | 10.8 |
| | | % injected dose | |
| Ex. 2 | Heart | 0.96 | 0.94 |
| | Liver | 20.45 | 1.62 |
| | | Counts/Gram ratio | |
| | Heart/Blood | 9.05 | 49.63 |
| | Heart/Muscle | 4.99 | 4.17 |
| | Heart/Liver | 0.57 | 7.26 |

TABLE VIII $[TcL_3]^+$ in Guinea Pigs

| Ligand | Organ or Ratio | 2 min p.i. | 60 min p.i. |
|---|---|---|---|
| | | % injected dose | |
| dmpe | Heart | 0.53 | 0.38 |
| | Liver | 38.0 | 36.8 |
| | | Counts/Gram ratio | |
| | Heart/Blood | 0.42 | 3.27 |
| | Heart/Muscle | 6.11 | 4.12 |
| | Heart/Liver | 0.30 | 0.13 |
| | | % injected dose | |
| Ex. 1 | Heart | 0.98 | 0.83 |
| | Liver | 24.0 | 13.3 |
| | | Counts/Gram ratio | |
| | Heart/Blood | 1.63 | 10.5 |
| | Heart/Muscle | 8.18 | 4.29 |
| | Heart/Liver | 0.82 | 0.72 |
| | | % injected dose | |
| Ex. 2 | Heart | 0.96 | 0.43 |
| | Liver | 24.85 | 26.13 |
| | | Counts/Gram ratio | |
| | Heart/Blood | 1.59 | 7.82 |
| | Heart/Muscle | 9.19 | 4.60 |
| | Heart/Liver | 0.51 | 0.30 |

C. SYNTHESIS OF BACKBONE-SUBSTITUTED DIPHOSPHINE LIGANDS

EXAMPLE 8

Preparation of Bis(dimethylphosphinomethyl)ether.

(i) Bis(bromomethyl) ether

This was prepared by the method of Stephen et al, *J. Chem. Soc.*, 1920, 117, 515.

(ii) Bis(dimethylphosphinomethyl) ether

To a solution of dimethylphosphine (5 g) in diethyl ether (110 cm$^3$) at $-70°$ C. was added portions of a solution on n-butyl lithium (2.5M in hexanes) until formation of the phosphide anion was complete (as monitored by $^{31}$P nmr spectroscopy). The mixture was stirred for 10 minutes at −70° C. and bis(bromomethyl) ether (5 g) then added. The mixture was allowed to warm to room temperature and then stirred at this temperature for several hours. The resulting mixture was extracted with portions of dilute hydrochloric acid (2M) and the combined aqueous extracts washed with diethyl ether. The aqueous layer was slightly basified with aqueous sodium hydroxide (30%) and then extracted with chloroform. Removal of the solvent from the chloroform layer under reduced pressure (40° C. at 150 mmHg) gave the diphosphine (2.8 g) in a substantially pure state.

$\delta^{31}P$ (CDCl$_3$) −51.1.

$\delta^{13}C$ (CDCl$_3$) 10.0(d, J=12), 74.2(dd, J=11, 5).

EXAMPLE 9

Preparation of 1,3-Bis(dimethylphosphino)-2,2-bis(methoxymethyl)-propane (i) 1,3-Dibromo-2,2-bis(methoxymethyl)propane To 2,2-bis(bromomethyl)propane-1,3-diol (100 g) was added potassium bicarbonate (80 g) and dimethyl sulphate (170 g). The mixture was stirred and heated to 100° C. After about 30 minutes at this temperature the reaction became very vigorous (Care!). After a further 2 hours heating and stirring the mixture had become very viscous. The mixture was cooled, made slightly basic by the addition of sodium bicarbonate, and then extracted with chloroform (4×200 cm$^3$). The chloroform extracts were combined and the solvent removed under reduced pressure to give the crude product. Repeated distillation under reduced pressure gave the pure product (25 g) as a colourless liquid (b.p. 65°–70° C. at 0.1 mmHg).

$\delta^{13}C$ (CDCl$_3$) 34.9(x2). 43.7, 58.9(x2), 71.0(x2).

(ii) 1,3-Bis(dimethylphosphinyl)-2,2-bis(methoxymethyl) propane

To a stirred solution of dimethylphosphine (24 cm$^3$) in dry diethyl ether (150 cm$^3$) at −40° C. was added a solution of n-butyl lithium (44 cm$^3$, 2.5M in hexanes). After about 30 minutes the temperature had risen to −20° C. and 1,3-dibromo-2,2-bis(methoxymethyl)propane (15 g) was added, causing an exothermic reaction. The reaction mixture was allowed to warm to room temperature and then left stirring overnight. The ether solution was extracted with several portions of dilute hydrochloric acid (2M), the combined aqueous extracts basified with aqueous sodium hydroxide, and the liberated phosphines extracted with chloroform. Nmr spectroscopy showed the formation of both the required diphosphine and a substantial quantity of 2,2-bis(methoxymethyl)propyldimethylphosphine. Addition of excess aqueous hydrogen peroxide (6%) converted both phosphines to their corresponding oxides. The aqueous layer was then separated and evaporated under reduced pressure. The resulting viscous oil was purified by chromatography on Florisil using methanol/ethyl acetate mixtures as eluants. The pure 1,3-bis(dimethylphosphinyl)-2,2-bis(methoxymethyl)propane (2.8 g) was isolated as a semicrystalline material.

$\delta^{31}P$ (CDCl$_3$) 41.8.

$\delta^{13}C$ (CDCl$_3$) 19.4(d, J=69), 19.45(d, J=69), 33.9(dd, J=68, 5), 43.1(t, J=5) 58.7(s), 58.7(s), 75.5(t, J=8).

(iii) 1,3-Bis(dimethylphosphino)-2,2-bis(methoxymethyl) propane

The previously prepared bis(phosphine oxide) (2.7 g) was added to lithium aluminium hydride (3.0 g) in dioxan (200 cm$^3$) and the mixture heated under reflux for 2.5 hours. After cooling, the mixture was hydrolysed by the careful addition of aqueous dioxan (25 cm$^3$, 1:1), and then aqueous sodium hydroxide (4 cm$^3$, 50%) was added. The resulting mixture was filtered and the bulk of the solvent then removed under reduced pressure (60° C. at 100 mmHg) to give the diphosphine. $^{31}P$ nmr showed no presence of other phosphorus-containing components.

$\delta^{31}P$ (CDCl$_3$/dioxane) −63.

$\delta^{13}C$ (CDCl$_3$) 15.7(m), 38.3(dd, J=16, 10), 42.2(t, J=10), 58.7(s), 76.7(t, J=9).

The diphosphine was converted to its crystalline disulphide derivative for analysis. Found: C, 41.9; H, 8.3. $C_{11}H_{26}O_2P_2S_2$ requires C, 41.75; H, 8.3%.

EXAMPLE 10

Preparation of 1,3-Dimethoxy-1,3-bis(dimethylphosphino) propane (i) 1,3-Dichloro-1,3-dimethoxypropane To a stirred quantity of 1,1,3,3-tetramethoxypropane (10 g) was cautiously added thionyl chloride (10 g) over a period of 10 minutes. The reaction was then stirred at room temperature until the reaction was complete (as indicated by nmr spectroscopy). The excess thionyl chloride was removed under reduced pressure (20 mmHg) and the residue distilled to give the dichloride (7.7 g) (b.p. 40° C. at 5 mmHg). Nmr spectroscopy showed the presence of approximately equal quantities of two diastereoisomers.

$\delta^{13}C$ (CDCl$_3$) 48.3(x2), 48.7(x2), 57.5(x4), 96.2(x2), 96.4(x2).

This material was found to deteriorate on standing and it was therefore prepared immediately prior to use.

(ii) 1,3-Dimethoxy-1,3-bis(dimethylphosphino)propane

To a stirred solution of dimethylphosphine (18 cm$^3$) in hexane (150 cm$^3$) at −50° C. was added a solution of n-butyl lithium (37 cm$^3$, 2.5M in hexanes). As the phosphide anion precipitated the mixture became very viscous and difficult to stir. After about 15 minutes 1,3-dichloro-1,3-dimethoxypropane (7.7 g) was added and the mixture allowed to warm to room temperature. The viscous mixture was agitated by bubbling dry nitrogen and then allowed to stand overnight. The resulting mixture was extracted with portions of dilute hydrochloric acid (2M), the combined aqueous extracts basified with aqueous sodium hydroxide solution, and the liberated phosphines extracted into chloroform. Removal of the chloroform under reduced pressure gave a mixture of the two diastereoisomers of 1,3-dimethoxy-1,3-bis(dimethylphosphino)propane in a satisfactory yield.

$\delta^{31}P$ (CDCl$_3$) −43.6 and −44.6.

$\delta^{13}C$ (CDCl$_3$) 8.2(d, J=14), 9.2(d, J=14), 9.4(x2)(d, J=14), 32.6(t, J=13), 32.8(t, J=13), 58.7−59.0(m), 79.0(dd, J=10, 8), 80.0(cc, J=12, 9).

EXAMPLE 11

Preparation of 1,3-bis(dimethylphosphino)-2-(2′-methoxyethoxymethyl)-2-(methoxymethyl)propane (i) 5,5-Bis(bromomethyl)-2-phenyl-1,3-dioxane 2,2-Bis(bromomethyl)propane-1,3-diol (250 g) and benzaldehyde (110 g) were added to benzene (500 cm$^3$) containing concentrated sulphuric acid (2 cm$^3$) and the mixture boiled. Water was removed using a Dean Stark apparatus. After about 6 hours the reaction was complete. The mixture was cooled and the sulphuric acid neutralised by the addition of excess sodium bicarbonate. The resulting solution was filtered and the benzene removed under reduced pressure to give an oil which solidified on standing. Recrystallisation from petroleum ether gave the 1,3-dioxane (296 g) as a white solid (m.p. 66° C.).

$\delta^{13}C$ (CDCl$_3$) 34.4, 36.0, 37.2, 71.7(x2), 102.1, 125.9(x2), 128.2(x2), 129.2, 137.2.

(ii) 5-Bromo-5-(2'-methoxyethoxymethyl)-2-phenyl-1,3-dioxane

Sodium (3.3 g) was added to 2-methoxypropanol (50 cm$^3$) and the mixture was then stirred and warmed until the metal had dissolved. 5,5-Bis(bromomethyl)-2-phenyl-1,3-dioxane (50 g) in 2-methoxypropanol (150 cm$^3$) was then added. The mixture was then boiled under reflux for 24 hours in an atmosphere of dry nitrogen. The excess 2-methoxypropanol was removed under reduced pressure and diethyl ether (550 cm$^3$) added. The sodium bromide was filtered off and the ether removed under reduced pressure to give the product as an oil (49.3 g, 95%). This material was sufficiently pure to be used in the subsequent reaction without further purification.

$\delta^{13}C$ (CDCl$_3$) 36.1, 38.3, 58.8, 70.7(x2), 70.9, 71.1, 71.6, 101.8, 125.8(x2), 128.0(x2), 128.8, 137.7.

(iii) 5-(2'-Methoxyethoxymethyl)-5-(methoxymethyl)-2-phenyl-1,3-dioxan

Sodium (1.4 g) was dissolved in dry methanol (20 cm$^3$) and placed in a Teflon-lined autoclave (Berghof, 150 ml) together with 5-bromo-5-(2'-methoxyethoxymethyl)-2-phenyl-1,3-dioxane (20 g) in dry methanol (30 cm$^3$). The reaction mixture was then heated at 150° C. for 6 days. The solvent was removed from the reaction mixture under reduced pressure and the organic residue taken up into ether. Sodium bromide was filtered off and the ether removed under reduced pressure to give the crude product (17 g). This material was sufficiently pure to be used without purification.

$\delta^{13}C$ (CDCl$_3$) 38.7, 58.8, 59.1, 69.8(x2), 70.9, 71.0, 71.2, 71.6, 101.5, 125.9(x2), 128.1(x2), 128.7, 138.2.

(iv) 2-(2'-Methoxyethoxymethyl)-2-(methoxymethyl)-propane-1,3-diol 5-(2'-Methoxyethoxymethyl)-5-(methoxymethyl)-2-phenyl-1,3-dioxan (17 g) was heated under reflux for 4 hours with a mixture of ethanol (130 cm$^3$), water (50 cm$^3$) and concentrated sulphuric acid (1.5 cm$^3$). The mixture was then cooled, neutralised by the addition of sodium bicarbonate, filtered and the volume reduced to about 50 cm$^3$ under reduced pressure. The aqueous residue was extracted with methylene chloride and the organic layer then dried over anhydrous sodium sulphate. Removal of the volatile components under reduced pressure gave an oil (9.5 g) which was shown to be largely the required diol. This was used without further purification.

$\delta^{13}C$ (CDCl$_3$) 44.9, 58.8, 59.4, 64.4(x2), 70.6, 71.5, 72.1, 74.3.

(v) 1,3-Dichloro-2-(2'-methoxyethoxymethyl)-2-(methoxymethyl)propane 2-(2'-Methoxyethoxymethyl)-2-(methoxymethyl) propane-1,3-diol (5.5 g), triphenylphosphine (24 g) and dry carbon tetrachloride were heated under reflux in an atmosphere of dry nitrogen until the reaction was complete (about 2.5 hours). The mixture was cooled, filtered and the solid residue washed with carbon tetrachloride. The carbon tetrachloride solutions were combined and the solvent removed under reduced pressure. Petroleum ether (250 cm$^3$, b.p. 40°–60° C.) was added to the residue and the resulting suspension filtered. Removal of the petroleum ether under reduced pressure gave the crude product (6 g) as an oil. The dichloride was isolated by chromatography on Kieselgel 60 (Merck) using ethyl acetate/petroleum ether mixtures as eluants. Final purification was achieved by distillation under reduced pressure. The pure dichloride (1.4 g) was isolated as an oil (b.p. 97° C. at 0.06 mmHg).

$\delta^{13}C$ (CDCl$_3$) 44.7(x2), 45.7, 58.8, 59.2, 68.9, 70.4, 70.8, 71.6.

(vi) 1,3-Bis(dimethylphosphino)-2-(2'-methoxyethoxymethyl)-2-(methoxymethyl)propane To a stirred solution of dimethylphosphine (5 cm$^3$), in dry liquid ammonia (80 cm$^3$) was added a solution of n-butyl lithium (10 cm$^3$, 2.5M in hexanes). This mixture was stirred at −60° C. for 10 minutes and 1,3-dichloro-2-(2'-methoxyethoxymethyl)-2-(methoxymethyl)propane (1.4 g) in a little dry diethyl ether was then added. The resulting mixture was stirred for 15 minutes at −60° C. and then allowed to warm up slowly to room temperature. When the ammonia had evaporated diethyl ether (150 cm$^3$) was added and the resulting mixture extracted with portions of dilute hydrochloric acid (2M). The combined aqueous extracts were basified with aqueous sodium hydroxide and the liberated phosphine extracted into chloroform. The solvent was removed from the combined chloroform extracts under reduced pressure to give the required phosphine (0.4 g).

$\delta^{31}P$ (CDCl$_3$) −63.1.

$\delta^{13}C$ (CDCl$_3$) 15.5(t, J=5), 15.9(t, J=5), 38.1(dd, J=16, 11), 42.2(t, J=10), 58.6(s), 58.8(s), 70.3(s), 71.6(s), 74.0(t, J=9), 76.5(t, J=9).

EXAMPLE 12

Preparation of 4,4-Bis(dimethylphosphinomethyl) tetrahydropyran (i) 4,4-Bis(ethoxycarbonyl)tetrahydropyran Sodium (10 g) was dissolved in dry ethanol (300 cm$^3$) and then diethyl malonate (30 g) was added slowly. After stirring for 15 minutes, bis(2-chloroethyl)ether (35 g) was added dropwise. The mixture was heated under reflux for 72 hours and then cooled to room temperature. After filtering the solvent was removed from the reaction mixture under reduced pressure to give the crude product. An initial purification was achieved by chromatography on alumina (activity 4) using ethyl acetate/petroleum ether mixtures as eluants. The pure product (11.3 g) was isolated by distillation under reduced pressure as an oil (b.p. 106°–108° C. at 0.03 mmHg).

$\delta^{13}C$ (CDCl$_3$) 13.8(x2), 30.8(x2), 52.1, 61.3(x2), 64.5(x2), 170.6(x2).

(ii) 4,4-Bis(hydroxymethyl)tetrahydropyran 4,4-Bis(ethoxycarbonyl)tetrahydropyran (11 g) in dry diethyl ether (50 cm$^3$) was added slowly to a stirred suspension of lithium aluminium hydride (2 g) in dry diethyl ether (15 cm$^3$) at a rate so as to maintain gentle boiling. Following the addition, the mixture was heated under reflux for a further 1 hour and then allowed to cool. Ethyl acetate (4 cm$^3$) was slowly added, followed by water (1.8 cm$^3$), then aqueous sodium hydroxide (1.8 cm$^3$), 15%, and finally a second portion of water (5 cm$^3$). The mixture was filtered and the solid washed with diethyl ether. The combined ether extracts were dried over anhydrous sodium sulphate and the ether then removed to give the diol (5.5 g).

δ¹³C (CDCl₃) 29.1(x2), 36.0, 63.3(x2), 67.4(x2).

(iii) 4,4-Bis(chloromethyl)tetrahydropyran 4,4-Bis(hydroxymethyl)tetrahydropyran (5.5 g), triphenylphosphine (19.8 g), dry carbon tetrachloride (100 cm³) and chloroform (15 cm³) were boiled together under reflux in an atmosphere of dry nitrogen until the reaction was complete (about 8 hours, as shown by nmr spectroscopy). The volatile components were removed under reduced pressure and the resulting solid mass extracted with petroleum ether (b.p. 40°-60° C.). Evaporation of the petrol from these extracts gave the crude dichloride. A sample of the pure dihalide (1.2 g) was obtained by vacuum distillation (b.p. 60° C. at 0.05 mmHg) followed by chromatography on Kieselgel 60 (Merck) using ethyl acetate/petroleum ether mixtures as eluants.

δ¹³C (CDCl₃) 31.4(x2), 37.2, 48.4(x2), 63.0(x2).

(iv) 4,4-Bis(dimethylphosphinomethyl)tetrahydropyran

To a stirred solution of dimethylphosphine (5-cm³) in dry liquid ammonia (60 cm³) was added a solution of n-butyl lithium (10.5 cm³, 2.4M in hexanes). After 10 minutes at 60° C. 4,4-bis(chloromethyl)tetrahydropyran (1 g), in a little diethyl ether, was added. After a further period of 15 minutes at low temperatures the mixture was allowed to warm up slowly to room temperature. When the ammonia had evaporated diethyl ether (150 cm³) was added and the resulting mixture extracted with dilute hydrochloric acid (2M). The combined aqueous extracts were basified with aqueous sodium hydroxide and the liberated phosphine extracted into chloroform. The solvent was removed from the combined chloroform extracts under reduced pressure to give the phosphine (0.3 g).

δ³¹P (CDCl₃) −62.5.

δ¹³C (CDCl₃) 15.7(x2)(t, J=4), 16.1(x2)(t, J=4), 34.7(t, J=12), 37.8(x2)(t, J=8), 43.4(x2)(dd, J=16, 12), 63.5(x2)(s).

EXAMPLE 13

By routes corresponding to those described in Examples 8 to 12, the following ligands were prepared.

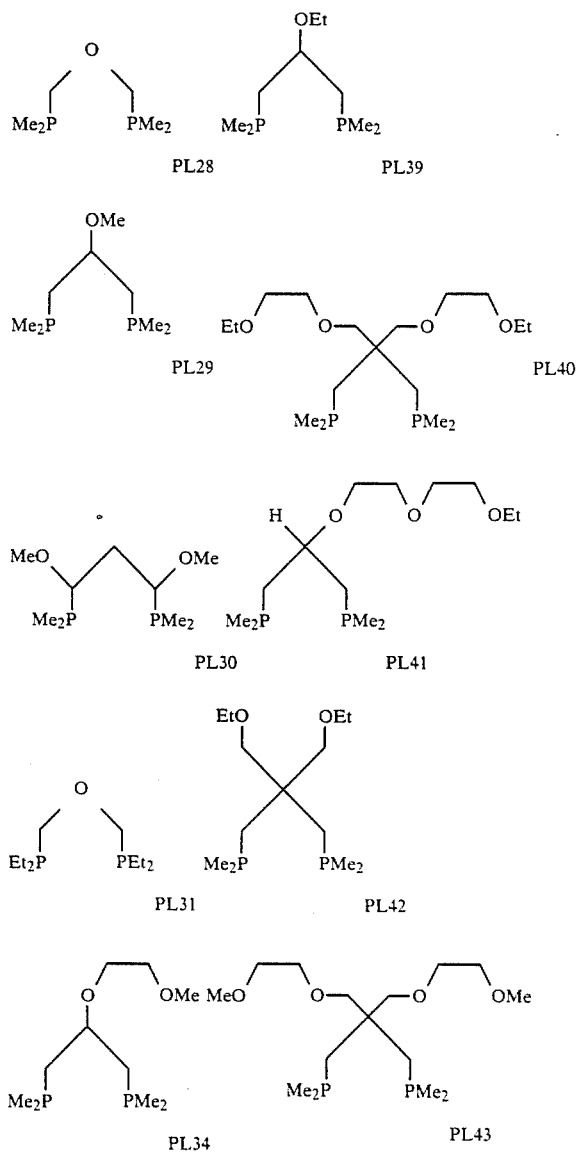

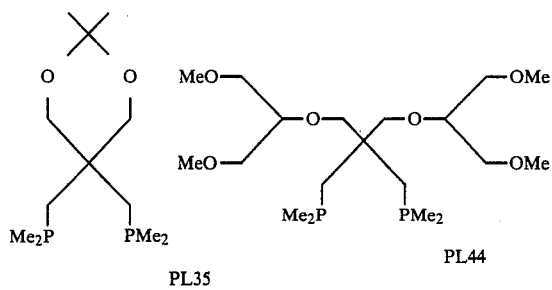
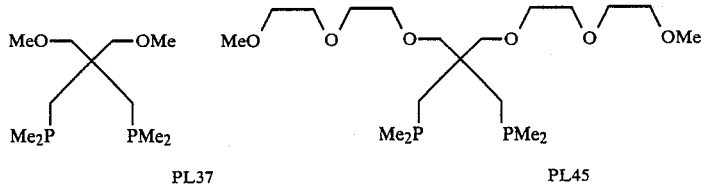
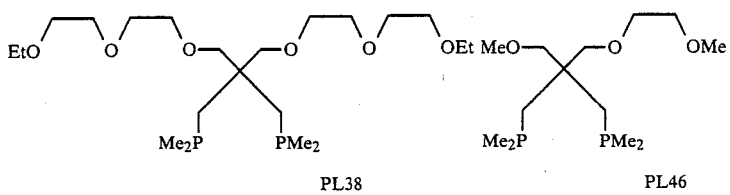
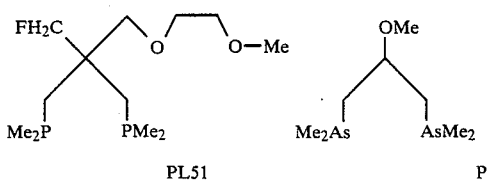
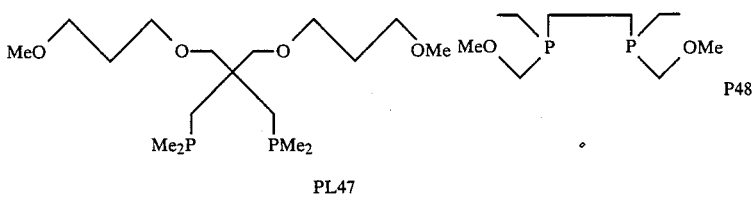
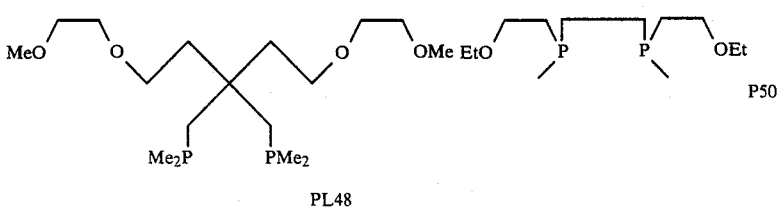
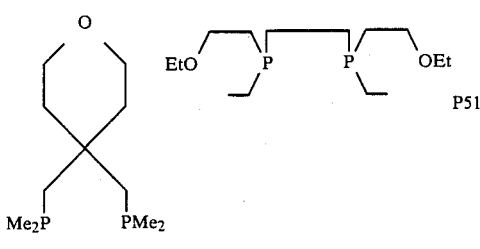

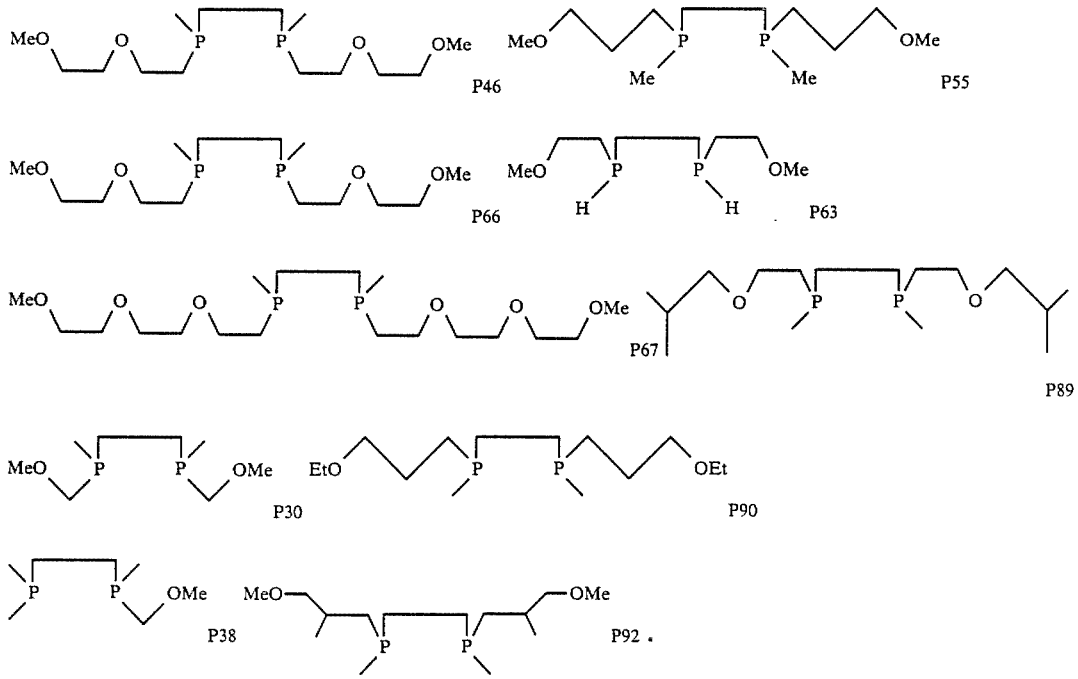

EXAMPLE 14

[Tc(I)L₃]⁺ Technetium I. Diphosphine complex

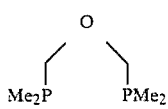

L = Ligand of Example 8

| Materials | | |
|---|---|---|
| 10 mg | Na₂S₂O₄ | |
| 1 ml | Saline | |
| 2 ml | EtOH | |
| 0.05 ml | 10M NaOH | |
| 20 μl | L | |
| 1 ml | $^{99m}$TcO₄⁻ Na generator eluate (at 2.9 GBq/ml) | |

Method

The components were mixed in a sealed, N₂ purged vial and heated at 120° C. for 30 minutes. After cooling, the pH was adjusted to 6.5 with 0.1M HCl and diluted with 4 ml of saline. The resulting solution was then submitted to chromatography analysis and animal biodistribution studies.

Chromatographic Data

The resulting preparation contains no free TcO₄⁻ or reduced technetium colloid, and indicates that the desired species is present in solution approximately 85% yield.

| | |
|---|---|
| Saline | rf = 0.09 |
| Methylethylketone | rf = 0.60 (broad) |
| Acetonitrile = Water 50:50 | rf = 0.90 |

HPLC Data

The complex elutes as a sharp band at approximately 18.3 minutes (~15% minor component at ~17.0 minutes).

Biodistribution Results

See Tables IX and X.

TABLE IX
ANIMAL BIODISTRIBUTION DATA - RAT

| Time p.i. in vivo | 2 min | | 60 min | |
|---|---|---|---|---|
| | % injected dose/organ | | | |
| | Mean | Std. dev. | Mean | Std. dev. |
| Heart | 0.84 | 0.07 | 0.35 | 0.01 |
| Blood | 3.23 | 0.06 | 0.39 | 0.02 |
| Muscle | 29.1 | 4.0 | 26.3 | 3.7 |
| Lung | 0.86 | 0.06 | 0.44 | 0.02 |
| Liver | 22.2 | 0.7 | 9.32 | 0.41 |
| Liver + GI | 37.0 | 1.3 | 8.52 | 4.66 |
| Kidney + Urine | 8.69 | 0.37 | 58.7 | 1.9 |
| Brain | — | — | — | — |
| | Counts/Gram ratio | | | |
| Heart/Blood | 3.92 | 0.67 | 13.6 | 1.1 |
| Heart/Muscle | 3.32 | 1.00 | 1.51 | 0.38 |
| Heart/Liver | 0.53 | 0.08 | 0.50 | 0.04 |
| Heart/Lung | 1.4 | 0.3 | 1.2 | 0.0 |

TABLE X
ANIMAL BIODISTRIBUTION DATA - GUINEA PIG

| Time p.i. in vivo | 2 min | | 60 min | |
|---|---|---|---|---|
| | % injected dose/organ | | | |
| | Mean | Std. dev. | Mean | Std. dev. |
| Heart | | | 0.18 | 0.03 |
| Blood | | | 1.39 | 0.43 |
| Muscle | | | 13.5 | 2.5 |

TABLE X-continued
ANIMAL BIODISTRIBUTION DATA - GUINEA PIG

| Time p.i. in vivo | 2 min | | 60 min | |
|---|---|---|---|---|
| | % injected dose/organ | | | |
| | Mean | Std. dev. | Mean | Std. dev. |
| Lung | | | 0.21 | 0.01 |
| Liver | | | 11.3 | 3.0 |
| Liver + GI | | | | |
| Kidney + Urine | | | 7.23 | 1.29 |
| Brain | | | 76.6 | 3.2 |
| Counts/Gram ratio | | | | |
| Heart/Blood | | | 3.58 | 1.47 |
| Heart/Muscle | | | 1.90 | 0.14 |
| Heart/Liver | | | 0.23 | 0.09 |
| Heart/Lung | | | 0.9 | 0.2 |

EXAMPLE 15

Synthesis of $[Tc(NO)X(L)_2]^+X^-$ Nitrosyl complex

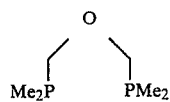

X=Cl

L=Ligand of Example 8

| Materials | | |
|---|---|---|
| $NH_2OH.HCl$ | = | 25 mg |
| $SnF_2$ | = | 1.0 ml at $6.6 \times 10^{-5}$M solution (aq). |
| L | = | 10 μl |
| $^{99m}TcO_4^-$-Na, 0.7 ml, generator eluate at 3.58 GBq/ml | | |
| Saline | | 0.3 ml |

Method

The components were mixed in a sealed, $N_2$ purged vial and heated at 120° C. for 1 hour. After cooling, the prep was filtered through a filter (an acrodisc 0.2 μm). The resulting solution was then submitted to chromatographic analysis and animal biodistribution study.

Chromatography

The resulting preparation contain no colloid or free $TcO_4^-$, and indicates that the desired species is present in approximately 90% yield.

| Saline | rf = 0.04 |
|---|---|
| Methylethylketone | rf = 0.62 |
| Acetonitrile:Water 50:50 | rf = 0.98 |

HPLC Data

The complex elutes as a sharp peak at approximately 17.4 minutes.

Gel Electrophoresis

The complex moves as a single band towards the cathode rf=−0.89 (− indicating movement towards cathode).

Biodistribution Results

See Table XI

TABLE IX
ANIMAL BIODISTRIBUTION DATA - RAT

| Time p.i. in vivo | 2 min | | 60 min | |
|---|---|---|---|---|
| | % injected dose/organ | | | |
| | Mean | Std. dev. | Mean | Std. dev. |
| Heart | 0.21 | 0.03 | 0.09 | 0.01 |
| Blood | 4.93 | 0.77 | 0.14 | 0.02 |
| Muscle | 19.5 | 1.4 | 7.0 | 0.2 |
| Lung | 0.70 | 0.06 | 0.09 | 0.01 |
| Liver | 26.1 | 0.7 | 5.72 | 1.31 |
| Liver + GI | 37.5 | 0.7 | 58.2 | 1.3 |
| Kidney + Urine | 18.7 | 1.8 | 30.3 | 1.2 |
| Brain | — | — | — | — |
| Counts/Gram ratio | | | | |
| Heart/Blood | 0.65 | 0.07 | 9.38 | 1.28 |
| Heart/Muscle | 1.21 | 0.15 | 1.37 | 0.19 |
| Heart/Liver | 0.10 | 0.01 | 0.19 | 0.05 |
| Heart/Lung | 0.5 | 0.1 | 1.5 | 0.2 |

EXAMPLE 16

Synthesis of $[Tc(L)_3]^+$ technetium (I) trisdiphosphine complex.

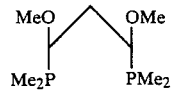

L=Ligand of Example 10.

| Materials | | |
|---|---|---|
| 2 ml | EtOH | |
| 1 ml | $SnF_2$ $2.64 \times 10^{-4}$M solution (aq). | |
| 10 μl | L | |
| 2 ml | $TcO_4^-$/Saline $^{99m}TcO_4^-$ Na generator eulate at 0.72 GBq/ml. | |

Methods

The components were mixed in a sealed, $N_2$ purged vial and heated at 120° C. for 1 hour. After cooling, the preparation was submitted for animal biodistribution studies.

Chromatography

The resulting preparation contains no colloid or free $TcO_4^-$, and indicates that the desired species is present in approximately 70% yield.

| Saline | rf = 0.02 |
|---|---|
| Methylethylketone | rf = 0.69 (70%) |
| | 0.03 (30%) |
| Acetonitrile:Water 50:50 | rf = 0.98 |

HPLC Data

The complete elutes as a single band with a retention of approximately 19.8 minutes (two minor components at 14 minutes and 18 minutes).

Gel Electrophoresis

The complex moves as a single band towards the cathode rf=−0.53 (with two minor components with rf=+0.04 and −1.07, where − indicates movement towards cathode).

Biodistribution Results

See Tables XII and XIII

TABLE XII
ANIMAL BIODISTRIBUTION DATA - RAT

| Time p.i. in vivo | 2 min | | 60 min | |
|---|---|---|---|---|
| | % injected dose/organ | | | |
| | Mean | Std. dev. | Mean | Std. dev. |
| Heart | 1.30 | 0.19 | 0.99 | 0.04 |
| Blood | 7.15 | 0.39 | 0.64 | 0.03 |
| Muscle | 29.1 | 2.9 | 17.1 | 5.3 |
| Lung | 3.57 | 0.18 | 1.79 | 0.54 |
| Liver | 17.4 | 0.9 | 8.81 | 0.97 |
| Liver + GI | 31.5 | 1.8 | 43.3 | 3.5 |
| Kidney + Urine | 9.33 | 1.34 | 25.7 | 1.0 |
| Brain | — | — | — | — |
| Counts/Gram ratio | | | | |
| Heart/Blood | 2.78 | 0.37 | 22.1 | 3.0 |
| Heart/Muscle | 5.01 | 0.72 | 6.4 | 1.65 |
| Heart/Liver | 1.14 | 0.24 | 1.64 | 0.21 |
| Heart/Lung | 0.5 | 0.1 | 0.7 | 0.2 |

TABLE XIII
ANIMAL BIODISTRIBUTION DATA - GUINEA PIG

| Time p.i. in vivo | 2 min | | 60 min | |
|---|---|---|---|---|
| | % injected dose/organ | | | |
| | Mean | Std. dev. | Mean | Std. dev. |
| Heart | | | 0.57 | -0.19 |
| Blood | | | 2.03 | 0.51 |
| Muscle | | | 20.7 | 5.7 |
| Lung | | | 1.01 | 0.24 |
| Liver | | | 10.0 | 0.7 |
| Liver + GI | | | 48.6 | 1.1 |
| Kidney + Urine | | | 23.3 | 4.0 |
| Brain | — | — | — | — |
| Counts/Gram ratio | | | | |
| Heart/Blood | | | 7.08 | 1.35 |
| Heart/Muscle | | | 3.98 | 1.26 |
| Heart/Liver | | | 0.94 | 0.04 |
| Heart/Lung | | | 0.4 | 0.1 |

EXAMPLE 17

$[Tc^INO(X)(L)_2]^+Cl^-$

X=Cl

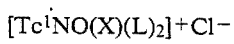
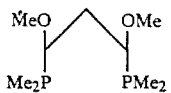

L = Ligand of Example 10

| Materials | |
|---|---|
| NH$_2$OH.HCl | 25 mg |
| SnF$_2$ | 1 ml of 6.6 × 10$^{-5}$ M solution |
| Saline | 2.0 ml |
| L | 10 µl |
| $^{99m}$TcO$_4^-$Na$^+$ | 2.0 ml Generator eluate (6.1 GBq/ml) |

Methods

The components were mixed in a sealed nitrogen purged vial, and heated at 120° C. for 1 hour. The cooled prepartion was filtered through 0.2 µm acros-. disc filter (Gelman) and diluted with 8 ml of saline. The resulting solution was submitted for chromatography analysis and animal biodistribution studies.

Chromatography

The resulting preparation contains no colloid and free TcO$_4^-$, and indicates that the desired species is present is approximately 80% yield.

| Saline | rf = 0.06 |
|---|---|
| Methylethylketone | rf = 0.74 (80%) |
| | 0.01 (20%) |
| Acetonitrile:water 50:50 | rf = 0.99 |

Gel Electrophoresis

The complex moves as a single band towards the cathode rf= −0.78, (− indicates movement towards cathode)

Biodistribution Results

See Tables XIV and XV

TABLE XIV
ANIMAL BIODISTRIBUTION DATA - RAT

| Time p.i. in vivo | 2 min | | 60 min | |
|---|---|---|---|---|
| | % injected dose/organ | | | |
| | Mean | Std. dev. | Mean | Std. dev. |
| Heart | | | 1.23 | 0.11 |
| Blood | | | 0.44 | 0.07 |
| Muscle | | | 22.9 | 2.7 |
| Lung | | | 0.72 | 0.12 |
| Liver | | | 6.03 | 0.54 |
| Liver + GI | | | 47.9 | 1.9 |
| Kidney + Urine | | | 15.8 | 1.1 |
| Brain | | | | |
| Counts/Gram ratio | | | | |
| Heart/Blood | | | 39.1 | 2.9 |
| Heart/Muscle | | | 5.51 | 0.89 |
| Heart/Liver | | | 2.47 | 0.11 |
| Heart/Lung | | | 2.7 | 0.3 |

TABLE XV
ANIMAL BIODISTRIBUTION DATA - GUINEA PIG

| Time p.i. in vivo | 2 min | | 60 min | |
|---|---|---|---|---|
| | % injected dose/organ | | | |
| | Mean | Std. dev. | Mean | Std. dev. |
| Heart | | | 0.70 | 0.06 |
| Blood | | | 1.31 | 0.13 |
| Muscle | | | 1.60 | 5.7 |
| Lung | | | 0.55 | 0.14 |
| Liver | | | 2.76 | 0.28 |
| Liver + GI | | | 57.1 | 5.0 |
| Kidney + Urine | | | 17.6 | 0.5 |
| Brain | — | | — | |
| Counts/Gram ratio | | | | |
| Heart/Blood | | | 13.9 | 2.2 |
| Heart/Muscle | | | 6.81 | 2.31 |
| Heart/Liver | | | 4.21 | 1.10 |
| Heart/Lung | | | 1.3 | 0.2 |

EXAMPLE 18

Synthesis of [Tc(I)(L)$_3$]$^+$ Technetium trisdiphosphine complex

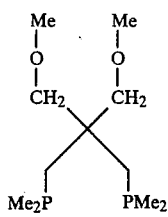

L = Ligand of Example 9

| Materials | | |
|---|---|---|
| EtOH | 0.5 ml | |
| Saline | 3 ml | |
| L | 10 μl | |
| $^{99m}$TcO$_4$Na | 0.3 ml | Generator eluate at 4.17 GBq/ml. |

Method

The components were mixed in a sealed, N$_2$ purged vial and heated at 120° C. for 1 hour. After cooling the preparation was submitted for chromatography analysis and biodistribution studies.

Chromatography

The resulting preparation contains no colloid or free TcO$_4^-$, and indicates that the desired species is present in approximately 90% yield.

| | |
|---|---|
| Saline | rf = 0.06 |
| Methylethylketone | rf = 0.72 |
| Acetonitrile:Water 50:50 | rf = 0.99 |

HPLC Data

The complex elutes as a broad band with a retention time of approximately 7.1 minutes.

Gel Electrophoresis

The complex moves as a single band towards the cathode rf = −0.27 (− indicates movement towards cathode).

Biodistribution results

See Tables XVI and XVII

TABLE XVI

| ANIMAL BIODISTRIBUTION DATA - RAT | | | | |
|---|---|---|---|---|
| | 2 min | | 60 min | |
| Time p.i. | injected dose/organ | | | |
| in vivo | Mean | Std. dev. | Mean | Std. dev. |
| Heart | 1.87 | 0.12 | 1.41 | 0.04 |
| Blood | 2.85 | 0.44 | 0.14 | 0.00 |
| Muscle | 26.3 | 5.4 | 19.4 | 2.6 |
| Lung | 2.59 | 0.31 | 0.75 | 0.17 |
| Liver | 16.3 | 1.1 | 2.45 | 0.90 |
| Liver + GI | 36.4 | 4.9 | 49.92 | 3.1 |
| Kidney + Urine | 10.6 | 1.1 | 12.2 | 2.1 |
| Brain | — | — | — | — |
| Counts/Gram ratio | | | | |
| Heart/Blood | 10.4 | 0.7 | 152 | 9.0 |
| Heart/Muscle | 8.45 | 1.2 | 8.36 | 1.59 |
| Heart/Liver | 1.68 | 0.22 | 8.42 | 3.86 |
| Heart/Lung | 1.2 | 0.2 | 3.2 | 0.6 |

TABLE XVII

| ANIMAL BIODISTRIBUTION DATA - GUINEA PIG | | | | |
|---|---|---|---|---|
| | 2 min | | 60 min | |
| Time p.i. | % injected dose/organ | | | |
| in vivo | Mean | Std. dev. | Mean | Std. dev. |
| Heart | 1.2 | 0.12 | 1.06 | 0.11 |
| Blood | 5.14 | 0.62 | 0.46 | 0.08 |
| Muscle | 27.4 | 8.7 | 23.7 | 2.8 |
| Lung | 1.65 | 019 | 0.56 | 0.06 |
| Liver | 17.3 | 2.8 | 2.6 | 0.25 |
| Liver + GI | 36.9 | 3.2 | 53.3 | 2.1 |
| Kidney + Urine | 14.5 | 1.6 | 15.0 | 1.0 |
| Brain | — | — | — | — |
| Counts/Gram ratio | | | | |
| Heart/Blood | 5.7 | 0.22 | 56.1 | 7.2 |
| Heart/Muscle | 6.5 | 2.49 | 6.14 | 1.07 |
| Heart/Liver | 1.12 | 0.07 | 5.63 | 0.36 |
| Heart/Lung | 0.6 | 0.1 | 1.9 | 0.3 |

EXAMPLE 19

Synthesis of [Tc$^I$(NC)X(L)$_2$]$^+$Cl Technetium Nitrosyl diphosphine complex

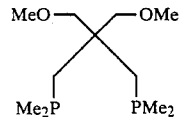

L = Ligand of Example 9

| Materials | | |
|---|---|---|
| NH$_2$OH.HCL | 25 mg | |
| Saline | 3.7 ml | |
| L | 10 μl | |
| $^{99m}$TcO$_4$Na | 0.3 ml | Generator eluate at 8.75 GBq/ml. |

Method

The components were mixed in a sealed, N$_2$ purged vial and heated at 120° C. for 1 hour. After cooling the preparation was filtered through 0.2 μm acrodisc (Gelman). The resulting preparation was then submitted for chromatography analysis and biodistribution studies.

Chromatography

The resulting preparation contains no colloid or free TcO$_4^-$, and indicates that the desired species is present in approximately 90% yield.

| | |
|---|---|
| Saline | rf = 0.01 |
| Methylethylketone | rf = 0.78 |
| Acetonitrile:Water 50:50 | rf = 0.99 |

HPLC Data

The complex elutes as a single band with a retention time of approximately 6.7 minutes (a minor component is at approximately 5.8 minutes)

Gel Electrophoresis

The complex moves as a single band towards the cathode rf= −0.64 (− indicates movement towards cathode).

Biodistribution results

See Tables XVIII and XIX

TABLE XVIII

ANIMAL BIODISTRIBUTION DATA - RAT

| Time p.i. in vivo | 2 min | | 60 min | |
|---|---|---|---|---|
| | % injected dose/organ | | | |
| | Mean | Std. dev. | Mean | Std. dev. |
| Heart | 1.56 | 0.02 | 1.47 | 0.15 |
| Blood | 2.05 | 0.33 | 0.14 | 0.09 |
| Muscle | 36.2 | 4.8 | 28.2 | 0.6 |
| Lung | 1.33 | 0.16 | 0.68 | 0.11 |
| Liver | 13.2 | 2.0 | 1.03 | 0.14 |
| Liver + GI | 35.3 | 1.4 | 45.5 | 2.2 |
| Kidney + Urine | 8.94 | 1.14 | 11.0 | 0.7 |
| Brain | — | — | — | — |
| | Counts/Gram ratio | | | |
| Heart/Blood | 10.9 | 0.8 | 192 | 97.2 |
| Heart/Muscle | 4.57 | 0.12 | 5.6 | 0.68 |
| Heart/Liver | 1.56 | 0.35 | 17.2 | 3.0 |
| Heart/Lung | 1.8 | 0.2 | 3.6 | 0.2 |

TABLE XIX

ANIMAL BIODISTRIBUTION DATA - GUINEA PIG

| Time p.i. in vivo | 2 min | | 60 min | |
|---|---|---|---|---|
| | % injected dose/organ | | | |
| | Mean | Std. dev. | Mean | Std. dev. |
| Heart | 1.36 | 0.10 | 1.05 | 0.10 |
| Blood | 3.77 | 0.81 | 0.48 | 0.05 |
| Muscle | 38.6 | 5.0 | 30.6 | 12.7 |
| Lung | 1.57 | 0.32 | 0.52 | 0.09 |
| Liver | 11.0 | 2.8 | 0.92 | 0.16 |
| Liver + GI | 35.0 | 2.9 | 45.9 | 3.4 |
| Kidney + Urine | 15.5 | 3.8 | 18.1 | 2.8 |
| Brain | — | — | — | — |
| | Counts/Gram ratio | | | |
| Heart/Blood | 8.66 | 1.26 | 49.6 | 3.2 |
| Heart/Muscle | 4.65 | 0.13 | 4.77 | 1.57 |
| Heart/Liver | 2.20 | 0.50 | 17.5 | 3.3 |
| Heart/Lung | 0.9 | 0.1 | 2.0 | 0.4 |

EXAMPLE 20

Synthesis of $[Tc(I)(L)_3]^+X^-$ Technetium (I) trisdiphosphine complex

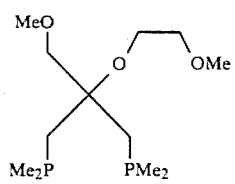

L=Ligand of Example 11.

| Materials | |
|---|---|
| EtOH | 0.5 ml |
| Saline | 3 ml |
| L | 15 μl |
| $^{99m}TcO_4Na$ | 0.35 ml Generator eluate at 4.26 GBq/ml. |

Method

The components were mixed in a sealed, $N_2$ purged vial and heated at 60° C. for 1 hour. After cooling the resulting preparation was submitted for chromatography analysis and biodistribution studies.

Chromatography

The resulting preparation contains no colloid or free $TcO_4^-$, and indicates that the desired species is present in approximately 90% yield.

| Saline | rf = 0.00 |
|---|---|
| Methylethylketone | rf = 0.71 |
| Acetonitrile:Water 50:50 | rf = 0.01 |

HPLC Data

The complex elutes as a single peak with a retention time of approximately 6.3 minutes.

Gel Electrophoresis

The complex moves eluates as a single band towards the cathode rf= −0.60 (− indicates movement towards cathode).

Biodistribution results

See Tables XX and XXI

TABLE XX

ANIMAL BIODISTRIBUTION DATA - GUINEA PIG

| Time p.i. in vivo | 2 min | | 60 min | |
|---|---|---|---|---|
| | % injected dose/organ | | | |
| | Mean | Std. dev. | Mean | Std. dev. |
| Heart | 1.21 | 0.35 | 1.03 | 0.11 |
| Blood | 2.81 | 0.11 | 0.46 | 0.12 |
| Muscle | 23.0 | 10.2 | 24.3 | 7.7 |
| Lung | 1.17 | 0.23 | 0.35 | 0.06 |
| Liver | 16.7 | 3.0 | 1.11 | 0.17 |
| Liver + GI | 46.3 | 4.1 | 50.8 | 5.8 |
| Kidney + Urine | 15.7 | 2.4 | 17.9 | 3.7 |
| Brain | — | — | — | — |
| | Counts/Gram ratio | | | |
| Heart/Blood | 11.9 | 1.3 | 55.8 | 10.3 |
| Heart/Muscle | 9.61 | 5.2 | 6.12 | 2.15 |
| Heart/Liver | 1.12 | 0.32 | 12.7 | 3.3 |
| Heart/Lung | 1.5 | 0.4 | 1.1 | 0.1 |

TABLE XXI

ANIMAL BIODISTRIBUTION DATA - RAT

| Time p.i. in vivo | 2 min | | 60 min | |
|---|---|---|---|---|
| | % injected dose/organ | | | |
| | Mean | Std. dev. | Mean | Std. dev. |
| Heart | 1.87 | 0.33 | 1.77 | 0.26 |
| Blood | 1.82 | 0.04 | 0.09 | 0.01 |
| Muscle | 34.3 | 10.8 | 33.9 | 0.5 |
| Lung | 1.38 | 0.21 | 0.51 | 0.14 |
| Liver | 14.9 | 3.4 | 1.66 | 0.10 |
| Liver + GI | 34.6 | 2.6 | 45.0 | 2.0 |
| Kidney + Urine | 8.59 | 2.28 | 12.0 | 1.3 |
| Brain | — | — | — | — |

TABLE XXI-continued

ANIMAL BIODISTRIBUTION DATA - RAT

| | Counts/Gram ratio | | | |
|---|---|---|---|---|
| Heart/Blood | 14.0 | 4.8 | 345 | 64.2 |
| Heart/Muscle | 5.73 | 2.5 | 6.58 | 0.85 |
| Heart/Liver | 1.82 | 0.97 | 17.1 | 3.6 |
| Heart/Lung | 1.3 | 0.4 | 4.8 | 0.9 |

EXAMPLE 21

Preparation of P46:
$(MeOC_2H_4OCH_2)MePC_2H_4PMe(CH_2OC_2H_4OMe)$

Reaction Scheme $Me(H)PC_2H_4P(H)Me \xrightarrow[petrol]{2n\text{-BuLi}} Li_2[MePC_2H_4PMe]$   (i)

$Li_2[MePC_2H_4PMe] \xrightarrow{2CH_3OC_2H_4OCH_2Cl} P46$   (ii)

Experimental

All reactions and manipulations were performed under vacuo or oxygen-free nitrogen atmosphere. Solvents were dried, and degassed by nitrogen purge prior to use. $CH_3OCH_2CH_2OCH_2Cl$ and n-BuLi were purchased from Aldrich. $Me(H)PC_2H_4P(H)Me$ was prepared according to a published method[1].

1. M Baake, O Stelzer, and V Wray. Chem.Ber. 113, 1356 (1980).

Procedure

In a 250 cm$^3$, 3-necked round bottomed flask, equipped with a dry ice condenser, pressure equallising dropping funnel and a teflon stirring bar, was placed in a solution of $Me(H)PC_2H_4P(H)Me$ (3.18 g, 26.06 mmol) in petrol (40°-60° C., 50 cm$^3$). To this solution was added n-BuLi (35 ml, 57.0 mmol, 1.6M in hexane) at −78° C. After warming back to room temperature a white precipitate was filtered and washed with petrol (40°-60° C., 2×25 cm$^3$). Sodium-dried liquid ammonia (150 cm$^3$) was then condensed into the above reaction vessel and an orange solution was formed. To this a solution of $CH_3OC_2H_4OCH_2Cl$ (6 cm$^3$, 52.1 mmol) in diethyl ether (20 cm$^3$) was added dropwise until the orange colour just disappeared. Then the ammonia was allowed to vaporise at ambient temperature. Diethyl ether (30 cm$^3$) was added to give a white suspension. This subsequently was hydrolysed, and the organic layer was separated and dried over anhydrous magnesium sulphate. Diethyl ether was removed by distilation at atmospheric pressure. The rest of the volatile materials were removed by distillation under vacuo at 120° C. The colourless liquid left was pure by NMR. Yield=4.7 g, 50.3%.

NMR $^{31}P\{H\}$ = −39.54 ppm and −39.65 ppm, singlets $^1H$ = 0.95 t(6H), $^2J$ P—H + $^5J$P—H = 3.0 Hz   = P—<u>Me</u>
    = 1.79 m (4H)   = P<u>C$_2$H$_4$</u>P
    = 3.37 p(6H)   = O<u>Me</u>
    = 3.48 m 8H,   = <u>OC$_2$H$_4$O</u>
    = 3.65 t(4H), $^2J$P—H + $^5J$P—H = 6.2 Hz   PC<u>H$_2$</u>O

EXAMPLE 22

$[Tc(P46)_3]^+$

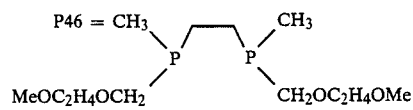

Materials 1.5 ml $SnF_2$ aqueous solution 32 μg per ml
2 ml Ethanol
0.05 ml 10M NaOH
10 μl P46
2 ml $Tc^{99m}O_4^{(-)}Na^{(=)}$ generator eluate at 1.78 GBq per ml

Method

The components were mixed in a sealed, $N_2$ purged vial and left standing at room temperature for 2 hours. Then pH was adjusted to 7 with diluted HCl acid (1M). The resulting solution was then submitted to chromatographic analysis and animal biodistribution study.

Chromatography Data

The resulting solution (above) contains no colloid or free $Tc^{99m}O_4^-$ and indicates that the Tc complex present in solution is approximately 70% pure.

| Saline | rf = 0.00 |
|---|---|
| Methyl Ethyl ketone | rf = 0.00 (30%) |
| | rf = +0.62 (70%) |
| Acetonitrile/water 50:50 | rf = +0.98 |

HPLC Data

The complex elutes as a sharp peak at approximately 6.7 minutes plus peaks at 5.5 and 6 minutes.

Gel Electrophoresis Data

The complex moved as a single band towards the cathode rf= −0.34 (− indicating movement towards cathode.

Biodistribution Results

See Tables XXII and XXIII.

Experimental and Chromatography, Electrophoresis, HPLC and in vivo biodistribution are exactly the same as previously described.

TABLE XXII

Animal Biodistribution Data (P46)
$[TcL_3]^+$ in rats L = P46

| | Time p.i. in vivo | | | |
|---|---|---|---|---|
| | 2 min | | 60 min | |
| | % injected dose/organ | | | |
| | Mean | Std. dev. | Mean | Std. dev. |
| Heart | 1.44 | 0.26 | 1.18 | 0.03 |
| Blood | 5.06 | 0.35 | 0.61 | 0.05 |

TABLE XXII-continued

Animal Biodistribution Data (P46)
$[TcL_3]^+$ in rats L = P46

| Muscle | 27.2 | 2.3 | 23.8 | 7.0 |
|---|---|---|---|---|
| Lung | 2.07 | 0.34 | 0.49 | 0.12 |
| Liver | 18.1 | 1.1 | 5.62 | 0.62 |
| Liver + GI | 35.1 | 2.8 | 48.2 | 5.6 |
| Kidney | 11.7 | 1.1 | 3.37 | 0.14 |
| Kidney + Urine | 11.8 | 1.2 | 17.3 | 2.4 |
| Brain | 0.05 | 0.00 | 0.02 | 0.00 |

| Counts/Gram ratio | | | | |
|---|---|---|---|---|
| Heart/Blood | 4.33 | 0.23 | 30.7 | 2.0 |
| Heart/Muscle | 6.04 | 1.11 | 6.39 | 2.64 |
| Heart/Liver | 1.13 | 0.25 | 2.82 | 0.28 |
| Heart/Lung | 1.1 | 0.1 | 4.3 | 0.9 |

TABLE XXIII

ANIMAL BIODISTRIBUTION DATA IN GUINEA PIG $[Tc(P46)_3]^+$

| Time in vivo | 2 min | | 60 min | |
|---|---|---|---|---|
| | Mean | Std. Dev. | Mean | Std. dev. |
| % injected dose/organ | | | | |
| Heart | 0.89 | | | |
| Blood | 1.89 | | | |
| Muscle | 31.9 | | | |
| Lung | 0.64 | | | |
| Liver | 7.03 | | | |
| Liver + GI | 39.8 | | | |
| Kidney | 9.31 | | | |
| Kidney + Urine | 19.9 | | | |
| Brain | 0.00 | | | |
| Counts/Gram ratio | | | | |
| Heart/Blood | 11.2 | | | |
| Heart/Muscle | 3.60 | | | |
| Heart/Liver | 1.74 | | | |
| Heart/Lung | 1.2 | | | |

EXAMPLE 23

$[TcCl_2L_2]^+$ Technetium III diphosphine dichloro complex

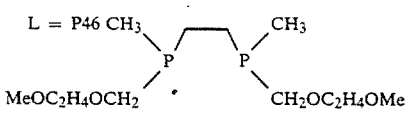

L = P46 CH₃\_/CH₃, P—P, MeOC₂H₄OCH₂/ \\CH₂OC₂H₄OMe

Materials

| 5 mg FeCl₃.6H₂O  |  | 15 mg EGTA |
| 2 ml Ethanol | added into | 100 mg NaCl |
| 10 μl P46 |  | 1.7 ml saline |
|  |  | 1.3 ml $^{99m}$TcO₄Na+ |
|  |  | generator eluate at 5.37 GBq/ml |

EGTA = Ethylene glycol - O,O'-bis(2 aminoethyl)-N,N,N',N'-tetraacetic acid.

Method

Firstly, the FeCl₃.6H₂O and P46 in ethanol were mixed in a P6 vial. A purple solution was formed instantaneously. Then this purple solution was transferred into a P11 vial which contained NaCl, EGTA, saline and $^{99m}$TcO₄⁻. The reaction mixture was then heated at 120° C. for 60 minutes (pH=4). The resulting solution was submitted to various analytical techniques, summarised as below:

Chromatography Data

The resulting solutions (above) contain no colloid or free $^{99m}$TcO₄⁻ and indicates that the technetium complex is present in solution in approximately 80% yield.

| Saline | rf = 0.01 |
| Methyl Ethyl ketone | rf = 0.59, 0.02 |
| Acetonitrile/water | rf = 0.99 |

HPLC Data

The complex elutes as a sharp peak at approximately 7.3 minutes, plus two small peaks at 5.2' and 6.1'.

Gel Electrophoresis Data

The complex moved as a single band towards the cathode rf=−0.67 (− indicating movement towards cathode).

Biodistribution Results

See Table XXIV.

TABLE XXIV

ANIMAL BIODISTRIBUTION DATA IN RAT $[TcCl_2(P46)_2]^+$ 'P46' = CH₃\_/ \_/CH₃, P—P, MeOC₂H₄OCH₂/ \\CH₂OC₂H₄OMe

| Time in vivo | 2 min | | 60 min | |
|---|---|---|---|---|
| | Mean | Std. Dev. | Mean | Std. dev. |
| % injected dose/organ | | | | |
| Heart | 1.48 | 0.23 | 1.26 | 0.17 |
| Blood | 4.70 | 0.14 | 0.47 | 0.20 |
| Muscle | 23.0 | 2.3 | 22.6 | 3.8 |
| Lung | 1.67 | 0.21 | 0.44 | 0.06 |
| Liver | 16.6 | 1.6 | 5.79 | 0.90 |
| Liver + GI | 34.6 | 3.1 | 38.6 | 0.6 |
| Kidney + Urine | 12.4 | 0.7 | 26.1 | 1.8 |
| Brain | 0.03 | 0.04 | 0.02 | 0.01 |
| Counts/Gram ratio | | | | |
| Heart/Blood | 4.49 | 0.48 | 47.2 | 17.3 |
| Heart/Muscle | 6.87 | 1.31 | 6.64 | 1.15 |
| Heart/Liver | 1.26 | 0.14 | 3.49 | 0.43 |
| Heart/Lung | 1.0 | 0.1 | 3.5 | 0.4 |

EXAMPLE 24

By methods generally as described in Examples 14 to 20, ligands listed in Example 13 were used to prepare cationic Technetium-99m complexes which were subjected to biodistribution testing in rats. The results are summarized in the following Tables XXV and XXVI.

TABLE XXV

RAT BIODISTRIBUTION RESULTS

| $[Tc^{(I)}L_3]^+$ | HEART | | HEART/BLOOD | | HEART/LIVER | |
|---|---|---|---|---|---|---|
| L | 2' | 60' | 2' | 60' | 2' | 60' |
| PL28 | 0.84 | 0.35 | 3.92 | 13.6 | 0.53 | 0.50 |
| PL29 | 1.30 | 0.92 | 2.92 | 34.3 | 0.98 | 1.81 |
| PL30 | 1.30 | 0.99 | 2.78 | 22.1 | 5.01 | 6.4 |
| PL31 | 0.77 | 0.05 | 1.61 | 1.37 | 0.39 | 0.03 |
| PL34 | 1.11 | 0.82 | 5.75 | 62.1 | 0.82 | 3.61 |
| PL35 | 0.88 | 0.55 | 4.07 | 35.3 | 0.46 | 1.65 |
| PL37 | 1.87 | 1.41 | 10.4 | 152 | 1.68 | 8.42 |
| PL38 | 1.31 | 1.01 | 18.8 | 156 | 0.78 | 3.79 |
| PL39 | 1.87 | 1.42 | 6.58 | 36.7 | 1.39 | 2.68 |
| PL40 | 1.21 | 0.82 | 5.68 | 106 | 0.54 | 2.23 |
| PL41 | 1.08 | 1.02 | 7.83 | 122 | 0.83 | 4.65 |
| PL42 | 0.96 | 0.76 | 2.35 | 56.0 | 0.38 | 1.47 |
| PL43 | 1.79 | 1.46 | 18.9 | 350 | 1.72 | 17.7 |

TABLE XXV-continued
RAT BIODISTRIBUTION RESULTS

| [TC(I)L3]+ | HEART | | HEART/BLOOD | | HEART/LIVER | |
|---|---|---|---|---|---|---|
| L | 2' | 60' | 2' | 60' | 2' | 60' |
| PL44 | 1.58 | 1.19 | 16.6 | 204 | 1.31 | 3.9 |
| PL45 | 0.62 | 0.40 | 5.90 | 94.1 | 0.26 | 2.74 |
| PL46 | 1.87 | 1.77 | 14.0 | 345 | 1.82 | 17.1 |
| PL47 | 1.20 | 1.15 | 5.33 | 113 | 0.64 | 2.49 |
| PL48 | 1.29 | 0.98 | 2.1 | 14.4 | 0.99 | 2.09 |

TABLE XXVI
RAT BIODISTRIBUTION RESULTS

| [TC(NO)L2Cl]+ | HEART | | HEART/ BLOOD | | HEART/ LIVER | |
|---|---|---|---|---|---|---|
| Ligand | 2' | 60' | 2' | 60' | 2' | 60' |
| PL28 | 0.21 | 0.09 | 0.65 | 9.38 | 0.10 | 0.19 |
| PL29 | 0.68 | 0.55 | 3.11 | 51.6 | 0.55 | 2.75 |
| PL30 | — | 1.23 | — | 39.1 | — | 2.47 |
| PL31 | 1.40 | 1.22 | 4.19 | 75.4 | 0.97 | 4.88 |
| PL34 | 0.48 | 0.19 | 0.60 | 6.52 | 0.28 | 0.56 |
| PL37 | 2.26 | 1.83 | 19.4 | 277 | 3.33 | 20.2 |
| PL38 | 1.12 | 0.65 | 4.55 | 62.9 | 0.64 | 1.05 |
| PL39 | 1.26 | 1.15 | 5.63 | 84.3 | 1.38 | 8.12 |
| PL40 | 1.30 | 1.01 | 10.3 | 83.4 | 0.9 | 3.88 |
| PL42 | 1.22 | 0.95 | 3.14 | 36.1 | 0.82 | 3.58 |
| PL43 | 0.83 | 0.59 | 3.60 | 40.6 | 0.49 | 0.89 |
| PL44 | 1.43 | 0.96 | 6.23 | 40.5 | 1.2 | 1.92 |
| PL45 | 0.46 | 0.22 | 1.14 | 6.84 | 0.18 | 0.36 |
| PL47 | 1.52 | 1.32 | 7.87 | 40.6 | 1.32 | 3.30 |
| PL48 | 0.66 | 0.51 | 1.00 | 1.99 | 0.4 | 1.07 |
| PL49 | 0.32 | 0.18 | 1.13 | 131 | 0.11 | 0.24 |

EXPERIMENTAL

The experimental techniques used to characterise and evaluate these new radiopharmaceutical complexes are outlined below:

Chromatography

Samples were supplied by needle approximately 2.5 cm from the bottom of two Gelman ITLC/SG strips (2.5 cm×20 cm) and one Whatman No. 1 strips (2.5 cm×20 cm) and then immediately placed in prepared ascending chromatography development tanks containing fresh solvent (1 cm): (a) saline, (b) methyl ethyl ketone, and (c) 50:50 acetonitrile:water respectively. After 15 cm elution the strips are removed, solvent fronts marked, dried and the distribution of activity determined using suitable equipment.

Electrophoresis

An 0.1 g agarose/10 cm³ phosphate buffer pH 7.4 gel was run at an applied potential of 300 V for approximately 35 mins, using bromophenol blue indicator (this indicator moves towards the cathode). The resulting distribution of activity was determined using suitable equipment.

HPLC

For Examples 3 to 7 and 18 to 23, a solvent gradient HPLC system was used, in conjunction with:
(a) 20 mM phosphate buffer pH 7.4
(b) Tetrahydrofuran (THF)
Samples are applied initially at 100% (a), the gradient changing to 100% (b) in approximately 17 minutes. Flow rate=2 ml/min Hamilton PRP column (15 cm×4.0 mm) ambient temperature. Identical HPLC systems were used for $^{99m}$Tc and $^{99}$Tc determinations, $^{99m}$Tc detected by emission, $^{99}$Tc detected via liquid scintillation method.

ANIMAL BIODISTRIBUTION

In vivo studies

In vivo biodistribution: 0.1 ml Tc$^{99m}$ prep was injected i.v. into a laterial tail vein of 6 anaesthetised rats.

At 2 minutes and 60 minutes post-injection, 3 rats were sacrificed by decapitation, bled from the neck and dissected. The following organs were removed at dissection: kidney; bladder(+ urine), lung, liver, spleen, stomach, small intestine, large intestine, brain (weighed), heart (weighed), thyroid and samples of blood (weighed) and muscle (weighed), the residual carcass and the tail (injection site). Subsequently samples were counted in an automatic twin crystal gamma counter.

Percentage biodistribution of injected material was calculated (after correction for background) for all organs using the formula:

$$\% \text{ injected dose} = \frac{\text{counts/organ}}{\text{total count in animal} - \text{count in tail}} \times 100$$

Since only samples of muscle and blood were taken, the percentage in these tissues was calculated assuming blood and muscle to represent 5.8 and 43% of total animal weight respectively using the formula:

$$\% \text{ injected dose} = \frac{\text{counts/organ}}{\text{total count in animal} - \text{count in tail}} \times 100$$

Since only samples of muscle and blood were taken, the percentage in these tissues was calculated assuming blood and muscle to represent 5.8 and 43% of total animal weight respectively using the formula:

$$\% \text{ injected dose in tissue} = \frac{\text{Counts/gram tissue} \times CF \times \text{Bodyweight} \times 100}{\text{Total counts in animal} - \text{total counts in tail}}$$

where CF=
0.058 for blood
0.43 for blood

References

1. Deutsch, E., Libson, K., Jurisson, S., Lindoy, L. F., Technetium Chemistry and Technetium Radiopharmaceuticals *Prog. Inorg. Chem.* 1982, Vol. 30, p. 175.

We claim:

1. A cationic complex of technetium 99 m having a formula selected from

[Tc(NO)$_n$X$_m$L$_2$]+A− and

[TcL$_3$]+A− where
X is a monodentate anionic ligand for Tc
A is an anion
n is 1 or 2 and m is correspondingly 1 or 0, and
L is a bidentate ligand having the formula: Y$_2$QZQY$_2$
where
each Q is phosphorus or arsenic, the groups Y may be the same or different and each is H or C1–C8 saturated hydrocarbon or saturated fluorohydrocarbon which may contain up to 3 ether oxygen atoms, Z is a —CC— or —CCC— or —COC— chain or o-phenylene which may be substituted by at least one C1–C8 saturated hydrocarbon or saturated fluorohydrocarbon group which may contain up to 3 ether oxygen atoms, provided that the ligand contains at least one —COC— ether linkage.

2. A complex as claimed in claim 1, wherein the groups Y may be the same or different and each is H or C1–C4 alkyl which may be substituted by C1–C4 alkoxy, Z is a —CC— of —CCC— or —COC— chain which may be substituted by C1–C4 alkoxy or alkoxyalkyl or spirocyclic ether.

3. A complex as claimed in claim 1, wherein each Q is phosphorus, Z is a —CC— or —CCC— chain, each Y is H, methyl, or methoxymethyl either provided that at least one Y is methoxymethyl, or one or more methoxymethyl or —COC— spirocyclic ether groups is attached to a carbon atom of Z.

4. A cationic complex as claimed in claim 1, having the formula:

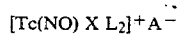

[Tc(NO) X L$_2$]$^+$A$^-$ where L is a ligand having the formula

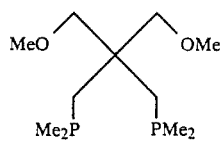

5. A cationic complex as claimed in claim 1, having the formula

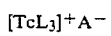

[TcL$_3$]$^+$A$^-$ where L is a ligand having the formula

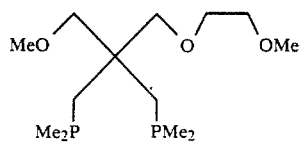

* * * * *